US010551393B1

(12) United States Patent
Thierer et al.

(10) Patent No.: US 10,551,393 B1
(45) Date of Patent: Feb. 4, 2020

(54) HIGH-THROUGHPUT, IN VIVO SCREENING PLATFORM FOR MODULATORS OF APOLIPOPROTEIN B

(71) Applicants: THE JOHNS HOPKINS UNIVERSITY, Baltimore, MD (US); CARNEGIE INSTITUTION OF WASHINGTON, Washington, DC (US)

(72) Inventors: James H. Thierer, Baltimore, MD (US); Steven A. Farber, Baltimore, MD (US)

(73) Assignees: CARNEGIE INSTITUTE OF WASHINGTON, Washington, DC (US); The Johns Hopkins University, Baltimore, MD (US)

( * ) Notice: Subject to any disclaimer, the term of this patent is extended or adjusted under 35 U.S.C. 154(b) by 413 days.

(21) Appl. No.: 15/611,780

(22) Filed: Jun. 1, 2017

Related U.S. Application Data

(60) Provisional application No. 62/347,178, filed on Jun. 8, 2016.

(51) Int. Cl.

| | |
|---|---|
| ***G01N 33/92*** | (2006.01) |
| ***C07K 14/46*** | (2006.01) |
| ***C12N 15/09*** | (2006.01) |
| *C12N 15/113* | (2010.01) |
| *A61K 38/00* | (2006.01) |

(52) U.S. Cl.
CPC .......... *G01N 33/92* (2013.01); *C07K 14/461* (2013.01); *A61K 38/00* (2013.01); *C12N 15/09* (2013.01); *C12N 15/113* (2013.01); *C12N 2310/14* (2013.01)

(58) Field of Classification Search
CPC ...... A61K 38/00; C07K 14/461; C12N 15/09; C12N 15/113; C12N 2310/14; G01N 33/92
See application file for complete search history.

(56) References Cited

PUBLICATIONS

Avraham-Davidi et al. “ApoB-containing lipoproteins regulate angiogenesis by modulating expression of VEGF receptor 1” Nature Med. 18:967-973 (2012).
Bedell et al. “In vivo genome editing using high efficiency TALENs” Nature 491:114-118 (2012).
Chen et al. “Zebraflash transgenic lines for in vivo bioluminescence imaging of stem cells and regeneration in adult zebrafish” Development 140:4988-4997 (2013).
Dahlem et al. “Simple methods for generating and detecting locus-specific mutations induced with TALENs in the zebrafish genome” PLOS Genetics 8:e1002861, 15 pages (2012).
England et al. “NanoLuc: A small luciferase is brightening up the field of bioluminescence” Bioconjug. Chem. 27:1175-1187 (2016).

(Continued)

*Primary Examiner* — Jeremy C Flinders
(74) *Attorney, Agent, or Firm* — Nixon & Vanderhye, P.C.

(57) ABSTRACT

We describe a high-throughput, phenotypic screening method for one or more modulator(s) of Apolipoprotein B (ApoB) in larval zebrafish. The modulator(s) may be enhancers or inhibitors of ApoB expression. This represents a remarkable opportunity to investigate drug targets in every cell and tissue type of a whole animal without bias, thus maximizing the likelihood of identifying viable pre-therapeutic leads for compounds or biologics in a subject (e.g., human).

17 Claims, 10 Drawing Sheets

Specification includes a Sequence Listing.

Donor Plasmid
Nano-Luc
STOP
Homology-Directed Repair
Zebrafish Genome
ApoB Gene
STOP
3′ UTR
TALEN Nuclease
Modified Zebrafish Genome
ApoB Gene
Nano-Luc
STOP
3′ UTR

(56) References Cited

PUBLICATIONS

Fang et al. "Zebrafish models of dyslipidemia: Relevance to atherosclerosis and angiogenesis" Transl. Res. 163:99-108 (2014).
Fang et al. "In vivo visualization and attenuation of oxidized lipid accumulation in hypercholesterolemic zebrafish" J. Clin. Invest. 121:4861-4869 (2011).
Hoshijima et al. "Precise editing of the zebrafish genome made simple and efficient" Dev. Cell 36:654-667 (2016).
Hwang et al. "Methods for targeted mutagenesis in zebrafish using TALENs" Methods 69:76-84 (2014).
Liu et al. "Apoc2 loss-of-function zebrafish mutant as a genetic model of hyperlipidemia" Dis. Model Mech. 8:989-998 (2015).
Macrae et al. "Zebrafish-based small molecule discovery" Chem. Biol. 10:901-908 (2003).
Neff et al. "Mojo Hand, A TALEN design tool for genome editing applications" BMC Bioinformatics 14:1, seven pages (2013).
Otis et al. "Zebrafish as a model for apolipoprotein biology: comprehensive expression analysis and a role for ApoA-IV in regulating food intake" Dis. Model Mech. 8:295-309 (2015).
Promega "Nano-Glo luciferase assay system" Technical Manual, 18 pages (2015).
Rennekamp & Peterson "15 years of zebrafish chemical screening" Curr. Opin. Chem. Biol. 24:58-70 (2015).
Shin et al. "Efficient homologous recombination-mediated genome engineering in zebrafish using TALE nucleases" Development 141:3807-3818 (2014).
Stacer et al. "NanoLuc reporter for dual luciferase imaging in living animals" Mol. Imaging 12:1-13 (2013).
Weber et al. "Genetic tools for multicolor imaging in zebrafish larvae" Methods 62:279-291 (2013).

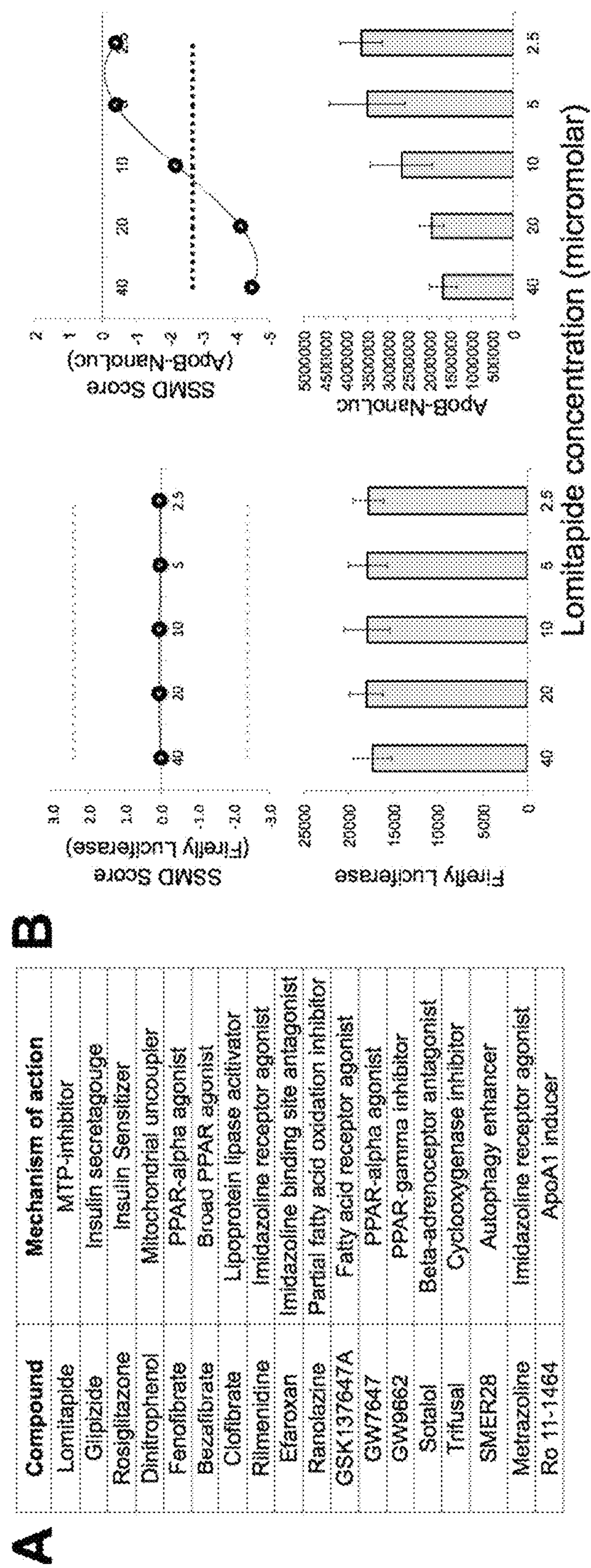

| Compound | Mechanism of action |
|---|---|
| Lomitapide | MTP-inhibitor |
| Glipizide | Insulin secretagouge |
| Rosiglitazone | Insulin Sensitizer |
| Dinitrophenol | Mitochondrial uncoupler |
| Fenofibrate | PPAR-alpha agonist |
| Bezafibrate | Broad PPAR agonist |
| Clofibrate | Lipoprotein lipase acitvator |
| Rilmenidine | Imidazoline receptor agonist |
| Efaroxan | Imidazoline binding site antagonist |
| Ranolazine | Partial fatty acid oxidation inhibitor |
| GSK137647A | Fatty acid receptor agonist |
| GW7647 | PPAR-alpha agonist |
| GW9662 | PPAR-gamma inhibitor |
| Sotalol | Beta-adrenoceptor antagonist |
| Triflusal | Cyclooxygenase inhibitor |
| SMER28 | Autophagy enhancer |
| Metrazoline | Imidazoline receptor agonist |
| Ro 11-1464 | ApoA1 inducer |

HIGH-THROUGHPUT, IN VIVO SCREENING PLATFORM FOR MODULATORS OF APOLIPOPROTEIN B

CROSS-REFERENCE TO RELATED APPLICATIONS

This application claims the benefit of U.S. Provisional Application No. 62/347,178, filed Jun. 8, 2017; the content of which is incorporated by reference in its entirety.

STATEMENT REGARDING FEDERAL GOVERNMENT SUPPORT

This invention was made at least in part with federal funds under NIH research project grants R01-DK111620 and R01-DK093399. The government has certain rights in the invention.

BACKGROUND OF THE INVENTION

Elevated serum Apolipoprotein B (ApoB) may represent a unifying risk factor underlying many of the world's most prevalent metabolic diseases. ApoB levels independently predict incidence of diabetes, metabolic syndrome, and cardiovascular disease even after adjusting for confounding variables. While it may seem implausible that a single disease marker could be implicated in such a broad range of diseases, the frequent clustering of these metabolic abnormalities is suggestive of shared causal risk factors. Also, the characterized roles of ApoB in lipid transport, endoplasmic reticulum stress, inflammation, and atherogenesis provide straightforward mechanistic connections to the etiologies of each linked metabolic disease. ApoB therefore represents a highly promising therapeutic target to combat the growing global burden of metabolic disease. Methods identifying agents that modulate the expression of ApoB must be developed to produce new pharmaceutical agents that prevent and/or treat these diseases.

SUMMARY OF THE INVENTION

We describe a high-throughput phenotypic screening method for one or more modulator(s) of Apolipoprotein B (ApoB) in larval zebrafish. In vivo screening avoids the disadvantages of cell-free and in vitro systems. This represents a remarkable opportunity to investigate drug targets in every cell and tissue type of a whole animal without bias, thus maximizing the likelihood of identifying viable pre-therapeutic leads for compounds or biologics in a subject (e.g., human).

One embodiment is a method of high-throughput, in vivo screening comprising the steps of: applying an agent to a zebrafish expressing an ApoB-reporter fusion protein, monitoring the reporter activity, comparing the reporter activity to a second reporter activity of a reference, and identifying a modulator of ApoB. It is preferred that an ApoB-reporter fusion protein is expressed from an ApoBb.1 locus-reporter gene, wherein the reporter is a luciferase. The methods of the present invention may be used to identify one or more modulator(s) of ApoB, which enhance ApoB expression when the reporter activity is greater than the second reporter activity of the reference. Moreover they may be used to identify one or more modulator(s) of ApoB, which inhibit expression of ApoB when the reporter activity is less than the second reporter activity of the reference. Suitable agents or entities used in the present invention include chemicals (e.g., low molecular weight); natural products; nucleic acids (e.g., RNAi, antisense, aptamer); proteins (e.g., agonist or antagonist based on native ligand of receptor, soluble receptor, antibody); and peptidomimetics. An example of a suitable fusion protein that is stably expressed by zebrafish of the present invention includes ApoB-NanoLuc® luciferase fusion protein expressed from a DNA sequence of SEQ ID NO: 3. An example of a protein sequence of a suitable fusion protein that is stably expressed by a zebrafish of the present invention is SEQ ID NO: 2.

Another embodiment of the present invention is a zebrafish comprising an ApoBb.1 locus-reporter fusion gene wherein a preferred reporter is luciferase such as an ApoBb.1 locus-NanoLuc® luciferase fusion gene of DNA sequence of SEQ ID NO: 3, and this zebrafish of the present invention may contain additional reporters whereby a genomic ubiquitous promoter drives expression of a firefly luciferase gene, a mCherry fluorescent reporter, or a combination thereof.

Another embodiment of the present invention is a method of high-throughput in vivo screening to identify a modulator of ApoB comprising the steps of: applying agents to zebrafish larvae expressing an ApoB-reporter fusion protein gene and a second reporter protein; monitoring the ApoB-reporter fusion protein and the second reporter protein activities; and comparing the reporter activities to the third reporter activities of a reference. It is preferred that the ApoB-reporter fusion protein is an ApoB-luciferase fusion protein expressed from an ApoBb.1 locus-NanoLuc® luciferase gene fusion. When monitoring protein activities it helps to sonicating the zebrafish larvae before measuring reporter activity. One suitable method of measuring reporter activity, such as an ApoB-fusion protein and/or of a second reporter protein, is by a high content screening (HCS) microscopy platform. A suitable second reporter is firefly luciferase.

The term "activity" refers to the ability of a gene or its product to perform a function, such as luciferase being able to catalyze a reaction to produce light. For example, an optical signal that can be quantified (e.g., light) may be preferred.

The term "ApoBb.1-NanoLuc® luciferase gene" is a DNA sequence comprising an ApoB promoter, ApoB gene or functional part thereof, fused to a NanoLuc® luciferase gene or functional part thereof as described below. FIG. 1 shows an example of such a gene fusion and corresponding protein fusion. The genomic ApoBb.1-NanoLuc® luciferase gene has a nucleotide sequence including introns and portions of the UTR that is at the native genomic locus of zebrafish and therefore contains all introns, untranslated regions, and cis regulatory elements of the native ApoBb.1 gene (SEQ ID NO: 3). The coding sequence (i.e., cDNA of spliced mRNA that will be translated to produce an ApoBb.1-NanoLuc® luciferase fusion protein) is SEQ ID NO: 1.

The term "ApoBb.1-NanoLuc® luciferase protein" refers to a protein having both ApoB activity and luciferase activity. An example of the amino acid sequence of such a protein is SEQ ID NO: 2.

The term "express" refers to the ability of a gene to express the gene product including for example its corresponding mRNA or protein sequence (s).

The term "luciferase" refers to an enzyme that produces bioluminescence such as NanoLuc® luciferase or firefly luciferase as examples. The term "NanoLuc" is the tradename of a luciferase that is specific to a NanoLuc® enzyme developed by Promega, referred to as "NanoLuc® luciferase."

The term "reference" refers to a standard or control conditions such as a sample (e.g., zebrafish that does not contain the reporter gene or express its reporter gene product, human cells), a subject that is free, or substantially free, of agent or entity.

The term "reporter gene" or "reporter" refers to a gene attached to a regulatory sequence of another gene of interest in bacteria, cell culture, animals, or plants. Certain genes are chosen as reporters because the characteristics they confer on organisms expressing them are easily identified (e.g., present or absent) and measured (e.g., quantification), or because they are selectable markers. Reporter genes are often used as an indication of whether a certain gene has been taken up by or expressed in the cell or organism population. Commonly used reporter genes that induce visually identifiable characteristics (e.g. optical signal measured by intensity or polarization) usually involve fluorescent and luminescent proteins. Examples include the gene that encodes jellyfish green fluorescent protein (GFP), which causes cells that express it to glow green under blue light, the enzyme luciferase, which catalyzes a reaction with luciferin to produce light, and the red fluorescent protein from the dsRed gene. Modified fluorescent and luminescent genes produce light having distinguishable maximal wavelengths, thereby enabling simultaneous identification and measurement of multiple different reporters.

BRIEF DESCRIPTION OF THE DRAWINGS

(FIG. 4A) Larval zebrafish were treated with various concentrations of lomitapide (an inhibitor of MTP) for 36 hours. (FIG. 4B) Larval zebrafish were fed a high-fat meal and then fasted for 0, 1, or 2 days.

(FIG. 7A) Z'-factor (Z') is shown for genetic negative and positive controls; pharmacological negative and positive (lomitapide) controls. (FIG. 7B) For humans treated with the strongest ApoB-lowering therapy available, Z' is shown for pharmacological negative and positive (lomitapide) controls; pharmacological negative and positive (a PCSK9 antibody) controls. (FIG. 7C) Z' is shown for genetic negative and positive controls; pharmacological negative and positive controls.

FIGS. 8A and 8B show validation of the screening assay protocol. (FIG. 8A) Compounds implicated in the regulation of lipid and lipoprotein metabolism are listed with their mechanism of action. (FIG. 8B) Lomitapide dose-responses. The hit selection cutoff is set to −2.7 (dashed).

(FIG. 9A) Lipoproteins of wild-type zebrafish were electrophoretically separated on a polyacrylamide gel, then detected by immersion in luciferase substrate. Mutant zebrafish lacking the ApoC2 gene were unable to lipolyze chylomicrons (CM) and very-low density lipoprotein (VLDL) particles into their smaller counterparts, intermediate density lipoproteins (IDL) and low-density lipoproteins (LDL). Conversely, zebrafish treated with lomitapide did not have large lipoprotein particles. (FIG. 9B) Immersion of transgenic zebrafish in luciferase substrate enabled visualization of ApoB-NanoLuc® luciferase within larvae.

DETAILED DESCRIPTION OF SPECIFIC EMBODIMENTS OF THE INVENTION

Figure 1:
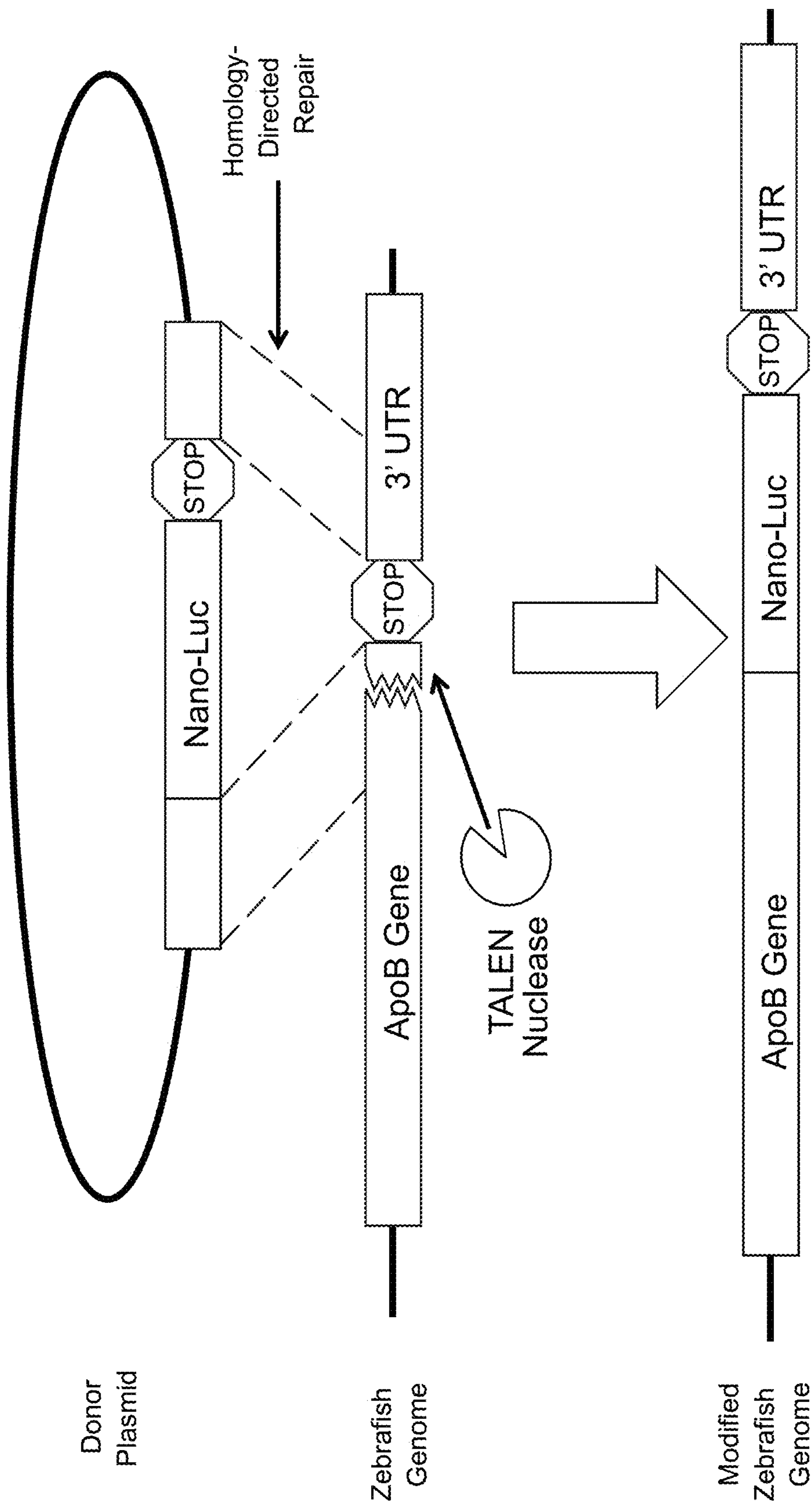
FIG. 1 shows a schematic of the generation of a genomic ApoB-NanoLuc® luciferase fusion protein. Specially designed TALEN nucleases introduce a double-stranded break just upstream of the stop codon of the Zebrafish ApoBb.1 gene. This lesion is repaired through homology-directed repair using the homology arms of the donor plasmid as a template, resulting in formation of the desired fusion construct between ApoB and NanoLuc® luciferase.

An in vivo high-throughput screening assay for modulators of ApoB in the larval zebrafish has been developed. For this purpose we have engineered the first ever transgenic zebrafish carrying a luciferase reporter fused to ApoB, which enables rapid and sensitive reporter quantification in 96-well plate format. We have shown that (i) the luciferase reporter does not interfere with ApoB function in vivo, (ii) the reporter shows the expected responses to physiological and pharmacological stimuli, and that (iii) the chemiluminescence assay used here shows substantial improvement in signal to noise and assay performance over any published large-scale screen in zebrafish.

The high-throughput screening (HTS) assay of the present invention has optimized the developmental stage of larvae used in the screen, (ii) modification of the robotics platform and optimization of buffer and treatment conditions to incorporate a homogenization step, and (iii) breeding of homozygous reporter lines for use in the primary screen. The high-throughput screen of the present invention screens the JHDL collection of 3,040 compounds utilizing a protocol for high-throughput screening in zebrafish called ARQiv-HTS (automated reporter quantification in vivo coupled to high-throughput screening robotics), with slight modifications to detect a chemiluminescent rather than a fluorescent readout. This quantitative HTS approach dispenses various dilutions of test compounds into wells containing individual larvae, which are subsequently quantified for ApoB levels using a plate reader. A counter-screening reporter has also been established that measures in parallel (dual-luciferase assay), which is used to exclude compounds that non-specifically reduce ApoB levels (e.g. cytotoxic and developmental delay responses).

An advantage of the JHDL is that many of the drugs have well-characterized targets, meaning that each hit implicates a corresponding target pathway as a regulator of ApoB. Putative pathways can be easily validated through treatment with known chemical probes to the putative target pathways. Modulation of ApoB is also likely to result in additional metabolic improvements, which can be assessed through a battery of secondary screens. Established fluorescent reporters of lipid transport, insulin signaling, atherogenesis, and inflammation can be assessed for responsiveness to lead compounds using high-content automated imaging, and resulting images are quantified using specialized statistical image analysis software. We have also developed a novel assay for monitoring lipoprotein size distribution that is included as an additional metabolic phenotype in the secondary screening process.

The luciferase used in the primary screening assay is the engineered NanoLuc® enzyme. This luciferase reporter is 100-fold brighter than the naturally occurring firefly or renilla luciferase enzymes. This increase in signal output provides a robust signal readout for the primary screening assay as well as the in-gel luciferase assay to detect lipoprotein size distribution for secondary hit validation screen. The NanoLuc® luciferase reporter is also significantly smaller than other frequently used fluorescent or bioluminescent reporters, reducing the likelihood that the tag disrupts native protein function.

Creation of NanoLuc® Luciferase-ApoB Fusion Knock-in Transgenic Line

ApoB has proven a difficult protein to study using traditional cloning and genome integration techniques due to its enormous size (approximately 14 kb of coding sequence, corresponding to a 540 kDa protein). Our early adoption of the recently developed precise genome engineering approaches in zebrafish have enabled us to develop the first fusion protein of ApoB ever reported, and one of the first endogenously tagged genes in the zebrafish genome.

Novel Quantitative Image Analysis Pipeline

The small size and optical clarity of the larval zebrafish has led to development of fluorescent reporters of numerous processes, as well as high-content screening (HCS) microscopy platforms capable of imaging them. For example, the VAST bioimaging platform (see the link WWW dot UNIONBIO dot COM slash VAST slash) provides unprecedented consistency and throughput for the imaging zebrafish and enables automated HCS. Our lab has developed improved methods for quantitative image analysis from whole-organism screening using principle component analysis (PCA) to quantify and cluster images into statistically different groups.

Use of the Larval Zebrafish in Whole-Organism Drug Screens In Vivo

The larval zebrafish model system provides the opportunity to study complex vertebrate disease phenotypes in the context of a highly tractable experimental system. Larval zebrafish are small, optically clear, develop rapidly, are easily bred in large numbers, can be consistently dosed with drugs placed directly in tank water, and are nourished by the maternally deposited yolk until about 5 days post-fertilization (dpf), making them ideal vertebrate systems for drug screens as well as whole-organism fluorescent imaging. Additionally, zebrafish have a proven track record in modeling human disease phenotypes, including several metabolic disease models such as diabetes, cardiovascular disease, and fatty liver disease. Thus, zebrafish have the potential to improve drug discovery by facilitating high-throughput phenotypic screening directly in living disease models.

Characterization of ApoB Paralogs in Zebrafish

As a first step in developing zebrafish as a model for studying the biology of ApoB, we have extensively characterized the phylogenetic history and expression pattern of the ApoB paralogs in zebrafish. In contrast to mammals, which have a single ApoB gene present in the genome, zebrafish possess 3 distinct paralogous ApoB genes named ApoBa, ApoBb.1, and ApoBb.2. Characterization of the evolutionary history (through phylogenetic and syntenic analysis), tissue specific expression pattern (through in-situ hybridization), and expression level of each of these paralogs (through RNA-seq and mass spectrometry) led the investigators to identify the ApoBb.1 gene as the predominant isoform of ApoB in zebrafish, individually accounting for approximately 95% of the ApoB mRNA and Protein expressed in the larval zebrafish. When ApoB is referred to in the application without the ApoBb.1 suffix, it is implied that this refers to the mRNA and protein derived from the ApoBb.1 locus in the zebrafish genome, rather than the ApoBa or ApoBb.2 genes or some combination of these genes.

Precise Fusion of NanoLuc® Luciferase to ApoBb.1 Locus

To overcome the difficulties of cloning the large ApoB gene and circumvent the complications of introducing transgenes into the genome, TALEN-mediated genome engineering was used to precisely integrate the NanoLuc® luciferase reporter as a fusion protein to the endogenous ApoBb.1 gene in zebrafish (see Shin et al. Development 141:3807-3818, 2014; Zu et al. Nature Methods 10:329-331, 2013; Neff et al. BMC Bioinformatics 14:1, 2013; Bedell et al. Nature 491: 114-118, 2012). Co-injection of TALEN mRNA targeted just upstream of the stop codon of ApoBb.1 and a donor construct containing the NanoLuc® luciferase coding sequence flanked by approximately 500 bp homology arms was used to generate mosaic founders. Putative integrants were raised to sexual maturity and outcrossed to wild-type (AB*) larvae, and the resulting progeny were screened for heterozygous carriers of the desired transgene. Sequencing of the target locus confirmed that the integration event was error-free and in-frame, and protein expression was verified through chemiluminescent detection of the reporter in transgenic larvae.

Validation of Wild-Type Function of Tagged ApoBb.1

Figure 2A:
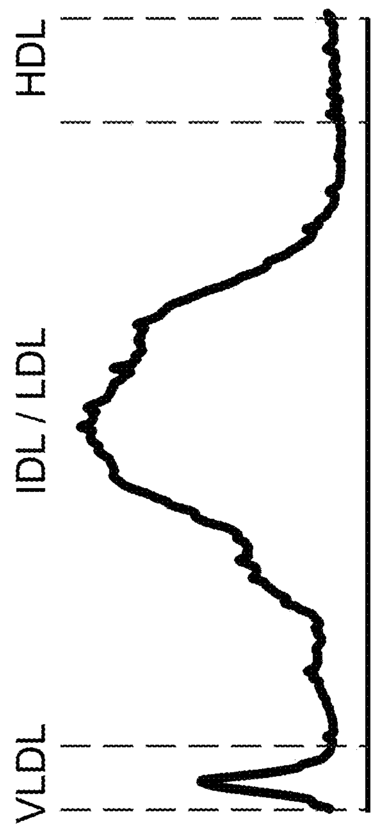
FIGS. 2A and 2B show lipoprotein size distributions detected by (FIG. 2A) in-gel luciferase assay and (FIG. 2B) fluorescent scan of BODIPY-stained adult zebrafish serum.
Figure 2B:
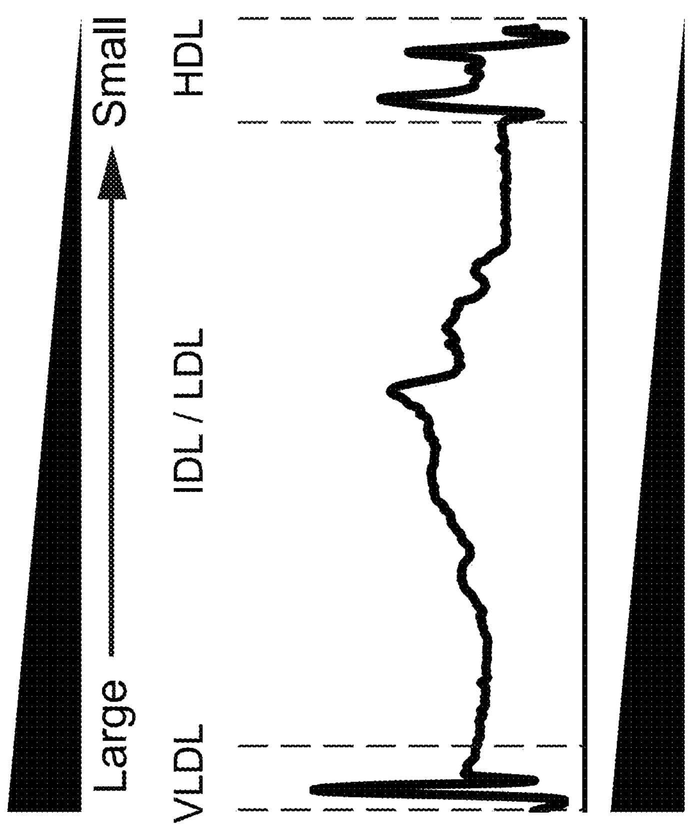

To evaluate whether introduction of the luciferase tag disrupted protein function, individual larvae carrying the reporter construct were homogenized and lipoprotein classes were separated on a 3% PAGE gel (see Singh et al. Lipids in Health and Disease 7:47, 2008). An in-gel luciferase assay was then performed to detect the NanoLuc® luciferase reporter present in the gel (FIG. 2A), and compared to the results obtained from adult zebrafish serum that was stained using lipophilic fluorescent dye (FIG. 2B). Encouragingly, essentially all of the signal was present in the expected VLDL, IDL, and LDL portions of the gel, which is consistent with the primary role of ApoB as an obligate structural component of lipid-rich lipoproteins. Additionally, this method has sufficient sensitivity and resolution to detect LDL subclasses, which are seen as deviations from the normal distribution in the plot profile. This indicates that the ApoB-luciferase fusion is lipidated, secreted, and processed in the pattern expected of native ApoB protein. Additionally, signal from the ApoB-luciferase fusion is responsive to known chemical and physiological modulators of ApoB (MTP inhibition and fasting).

Introduction of Counter-Screen Reporter

The primary screen seeks to identify compounds that lower ApoB levels, which is likely to identify numerous false positives that are cytotoxic or inhibit fundamental cellular processes such as transcription or translation. The inclusion of a counter-screen helps identify compounds that have strong effects on the target phenotype without causing major disruptions in other cellular processes. The pd75 zebrafish line carries a ubiquitous promoter driving firefly luciferase as well as the mCherry fluorescent reporter, which can be used to detect developmental delay or cytotoxicity in any organ. This line has been crossed to the ApoB reporter to generate double-transgenic zebrafish carrying both a ubiquitous firefly reporter and the ApoB reporter.

Independent Measurement of Multiple Luciferase Reporters in a Single Reaction

The Nano-Glo® dual luciferase assay provides the means to independently measure firefly and NanoLuc® luciferase in a single reaction enabling parallel measurement of the primary screen reaction and counter-screen reaction in a high-throughput compatible add-and-read format. Consistent measurement of luciferase activity requires homogenous sample inputs, so we have developed homogenization methods using a microplate sonicator that exceeds the throughput capacity of the plate reader.

Excellent Signal to Noise and Statistical Assay Performance

Figure 3:
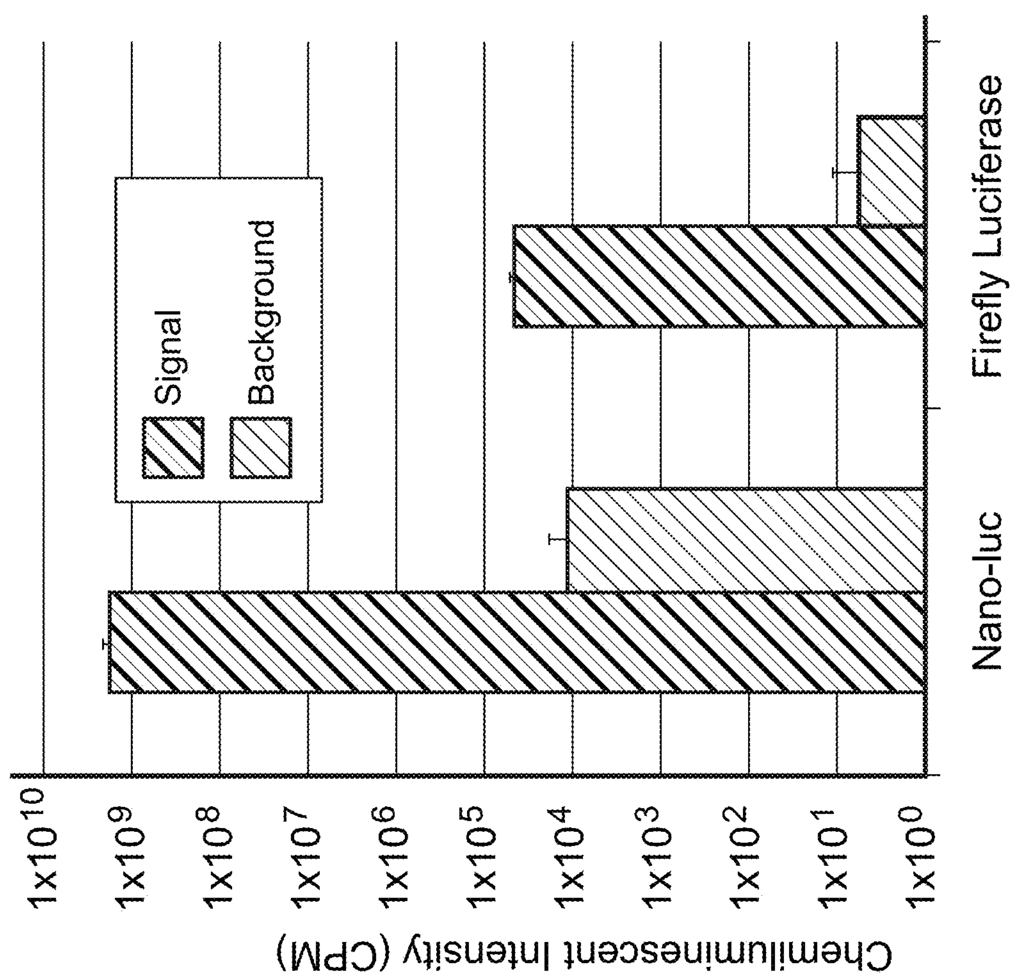
FIG. 3 shows signal and background measurements for the primary and counter-screen luciferase assays showing signal-to-background ratios of >10,000:1.

Signal to noise ratio: Luciferase reporters are essentially free of background noise, which has resulted in signal to background ratios between 100- and 2,000-fold higher than the best analogous fluorescent assays reported in zebrafish (FIG. 3).

Statistical Performance:

The most commonly used measure of HTS assay quality is the Z-factor (Z'). The Z' for the primary assay is 0.67 for the primary screen and 0.76 for the secondary screen using the signal to background ratios shown in FIG. 2, reflecting an "excellent" high-throughput assay that is well above the threshold of 0.5 for an HTS-ready assay.

Sample-Size and Hit Cutoff Calculation:

Although Z' is the most widely adopted statistical test to evaluate an assay for HTS, use of the strictly standardized mean difference (SSMD) is more appropriate for quality assessment and hit selection for drug screening in vivo as it accounts for unequal variance and outliers. To perform this statistical assessment on our assay, a titration test of lomitapide (the positive control drug treatment compound) was performed at 25, 10, 4, and 1.6 uM concentrations. This analysis determined that a sample size of 16 would be sufficient to detect compounds producing a small (25%) effect size relative to lomitapide control (Type I/II error rates of 0.01 and 0.001, respectively; $Z\alpha$ was 2.58; $Z\beta$ was 3.09). Using a sample size of 16, we then calculated a predicted SSMD score 'hit' cutoff, using bootstrapping with replacement on the lomitapide data, for detecting a 25% effect size. This analysis determined a score of >3.2 (or >3.6 for log transformed data) can be used to flag primary screen hits.

Figure 4B:
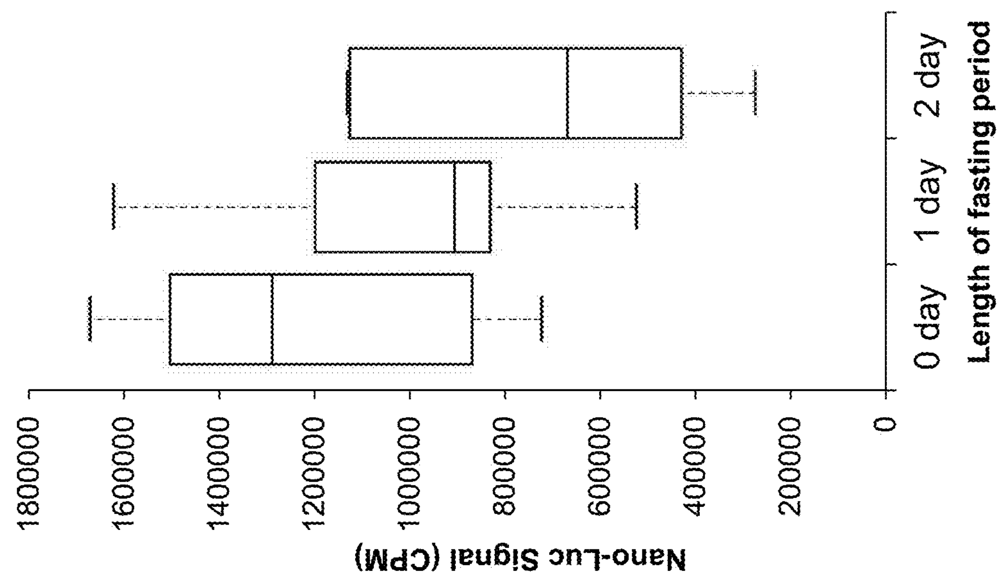
FIGS. 4A and 4B show dose-responses of ApoB reporter signal to established pharmacological and physiological modulators.
Figure 4A:
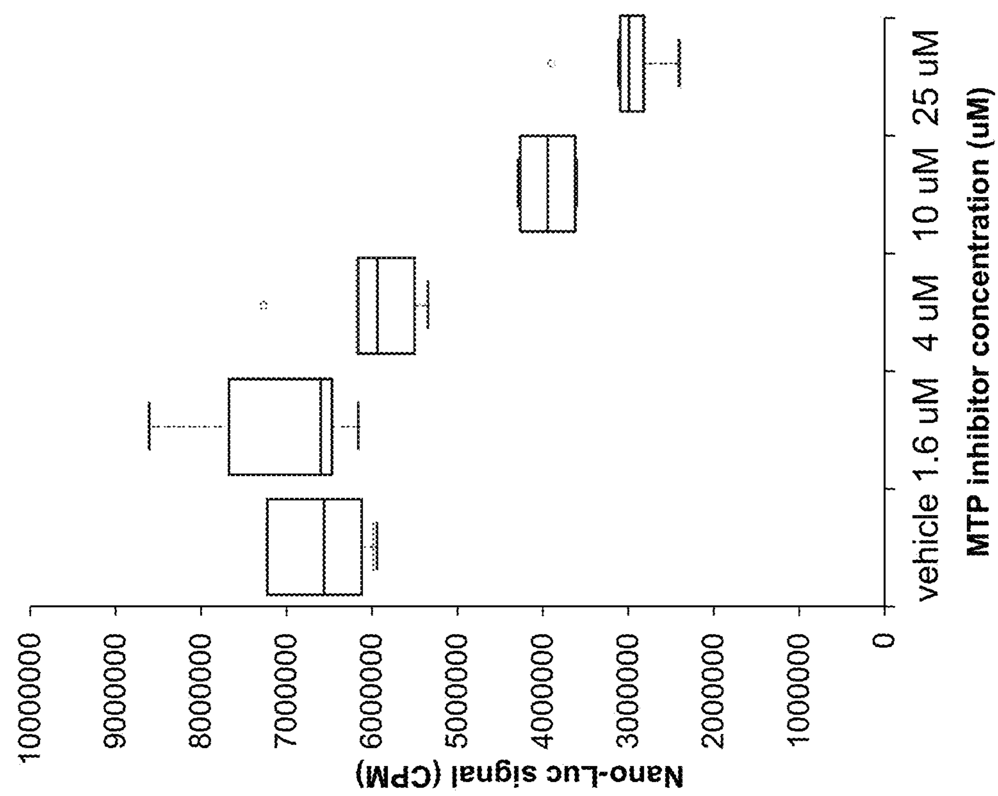

Proof of Principle Using Known Physiological and Pharmacological Modulators of ApoB Known modulators of ApoB can be used as a proof of principle to demonstrate the sensitivity of the screen as well as the validity of the experimental model. Of the two existing inhibitors of ApoB, lomitapide is the most appropriate for use as a proof of principle because it is a small molecule. Conversely, mipomersen is an injectable antisense biologic that is not suitable for comparison to small-molecule inhibitors and cannot be used a high-throughput manner. Larval zebrafish were treated with serial dilutions of the lomitapide for 36 hours from 2.5 to 4 dpf. Lomitapide treatment results in a dose-dependent reduction in reporter activity relative to vehicle-treated controls (FIG. 4A).

Given the paucity of pharmacological modulators of ApoB, we sought to further validate our model by assessing responsiveness of the reporter to known physiological perturbations. ApoB levels are elevated after feeding as dietary lipid is packaged into ApoB-containing lipoproteins and transported throughout the body, and are therefore inversely correlated to time since their last feed. Zebrafish were fed a high fat diet on 6 dpf, and either re-fed or fasted for 1 or 2 days. We observed the expected inverse relationship between the reporter signal intensity and the duration of the fast, indicating that the reporter construct is responsive to the expected physiological stimuli (FIG. 4B). The higher variability in the fasting experiment relative to the drug treatment is likely due to variations in food intake and behavior.

Threshold Justification for Primary Screening Assay

The inter-individual variation of ApoB levels in humans was used as a guide to determine a physiologically relevant effect size. A 12% change in ApoB corresponds to a one quintile shift in the population distribution, which was chosen as a good minimum threshold of detection. The percent effect threshold can be set as an arbitrary fraction of the effect size observed in positive control samples. As positive control treatment resulted in approximately a 50% reduction in ApoB levels, a 25% effect size relative to positive control treatment represents about a 12.5% absolute effect size, which was used in the sample size calculation above. Sensitivity to this relatively small effect size leaves a large pool of candidates that can be screened for combinatorial effects.

Assay Tolerance and Reproducibility

Control Parameters:

The Nano-Glo® dual-luciferase assay was developed by the Promega, which has provided detailed literature on the time and temperature dependencies of the assay (see WWW dot PROMEGA dot COM slash RESOURCES slash PROTOCOLS slash TECHNICAL-MANUALS slash 101 slash NANOGLO-DUAL-LUCIFERASE-REPORTER-ASSAY-PROTOCOL slash). The use of an automated assay enables precise control and monitoring of each of these parameters, neither of which are highly variable in the time and temperature ranges to be used in the screen.

Assay Tolerance:

Assay tolerance to DMSO was determined in the concentration range between 0.25 and 3%. In this concentration range, DMSO had no observable effect on signal. However, to avoid potential effects of DMSO alone on zebrafish physiology, the maximal final concentration is 0.1%.

Assay Reproducibility:

There was no significant variation between plates, position within the plate, and experiments performed on different days.

Assay Optimization for High-Throughput Screening

Preliminary results show that the assay is not disruptive to zebrafish metabolism, is responsive to expected physiological and pharmaceutical treatments, is statistically robust, and compatible with existing automated high-throughput screening platforms.

Determine Optimal Time Point for Cessation of Drug Treatment

Zebrafish are nourished by maternal yolk for approximately the first 5 days of development, which provides a period of highly consistent nutrient levels between individual larvae that is amenable to high-throughput screening of metabolic phenotypes. Drug treatment commences a 3 dpf after the liver has differentiated, and the endpoint of drug treatment is optimized empirically by monitoring ApoB production throughout zebrafish development. ApoB levels are measured in developing zebrafish every 12 hours and assess responsiveness to lomitapide treatment to determine the relative rates of ApoB production at each time point. Cessation of drug treatment and reporter quantification just prior to the onset of the fasted state in the pilot screen maximizes the exposure time for each compound and target the full repertoire of larval organs while avoiding the complications of studying fasted zebrafish.

Modify Robotics Footprint to Incorporate Larval Homogenization

The luciferase assay requires larval homogenization prior to reporter quantification. The microplate sonication protocol we have developed provides consistent tissue disruption in low throughput, but needs to be assessed for consistent performance in high-throughput capacity as it is required to process hundreds of plates per day.

Breed and Raise Zebrafish Carrying Homozygous Primary and Counter-Screening Reporters The ApoB-NanoLuc® luciferase reporter line to be used for the primary screen and the ubi-Fluc line for the counter screening assay have already been developed, but zebrafish homozygous for both reporters are used to ensure true-breeding and produce large numbers of offspring. Heterozygotes for each reporter have been crossed and are being raised to sexual maturity, and a subsequent in-cross of the double-heterozygous fish are used to generate fish that are homozygous for both transgenes. The stock is then expanded and used to generate the large numbers of offspring for the screen.

Screen the JHDL Collection of 3,040 Compounds

Execution of the screen relies on a versatile and rapid reporter-based whole-organism screening platform, termed ARQiv (Automated Reporter Quantification in vivo. Recently combined with a customized robotics work station, this methodology achieves true high-throughput screening rates in vivo (now termed, ARQiv-HTS). Our screen is a modification of this method because the luciferase reporter requires homogenization of the sample and addition of substrate prior to quantification.

Library Selection

The JHDL is comprised of 3,040 compounds, the majority of which are approved for human use and have characterized molecular mechanism(s) of action. This library offers several advantages; first it maximizes likelihood of identifying positive hits from a relatively small compound library as it is validated against all major drug-target classes. Second, the characterized targets enable straightforward identification of genes and pathways involved in the regulation of ApoB. Lastly, hits from this screen can progress rapidly through clinical trials as they are already approved for human use, which has proven to be an effective strategy in drug repurposing.

Quantitative High-Throughput Screening (qHTS)

We employ a quantitative HTS strategy whereby each compound is tested over a dilution series. This approach has been shown to reduce false-positive and false-negative rates as a posteriori validation is provided where graded effects are evident across the titration curve, whereas potentially spurious results are revealed by effects at only a single concentration. Following the recommendations of ARQiv-HTS and power calculations outlined in preliminary data, the screen uses 16 biological replicates and test six serial 1:2 dilutions, testing a concentration range from 0.125 μM to 4 μM. This corresponds to one compound being tested per plate, and the established plate read capacity of 500 plates per day therefore enables testing of 500 compounds in a single day, requiring ~48,000 larvae.

Large-Scale Egg Production

Customized mass fish breeding chambers are used to produce the large number of transgenic reporter larvae needed for screening. The chambers contain gridded plastic canvases (e.g., Darice, #33900-200) that allow fertilized eggs to descend to a middle chamber where they are collected on a floor of nylon mesh that allows water to flow through the tank while eggs are being collected. Each chamber produces approximately 10,000 eggs per day. Six such tanks can be dedicated to the screen to meet the minimal requirement of 48,000 eggs per day.

Large-Scale Fish Sorting and Dispensing

Complex Object Parametric Analyzer and Sorter (COPAS, Union Biometrica) is used to batch sort viable embryos at 1-2 dpf and to sort viable larvae into 96-well insert plates at later stages (as per prior ARQiv-HTS assays, Wang et al., 2015).

Compound Dispensing and Titration

Hudson Robotics Automated Workstation custom-designed to accommodate ARQiv-based screening and serves all automated handling of compounds, barcoding/reading, and multiwell insert/plate transfers downstream of COPAS dispensing. This includes automated rinse, feed, and anesthetic treatments facilitated by the multiwell inserts.

One Embodiment of a Screen (Outline):

0 dpf: Eggs from are collected and placed in growth media.

1-4 dpf: COPAS batch sorts embryos/larvae each day for viability 4-5 dpf: Viable larvae are treated with test compounds in barcoded plates for 24 hours.

5 dpf: ARQiv-HTS is used to quantify primary and counter screen signal

Confirmation and Retests

All retesting uses the primary screen procedure except that compounds producing maximal effects at the periphery of the dilution series can be retitrated—centering the effective concentration within the dilution series. Consistently significant results indicate confirmed hits and all others are discarded.

One Embodiment of an Orthogonal Secondary Validation Screen Filter for Inhibitors of NanoLuc® Enzyme Another potential source of false positives are inhibitors of the NanoLuc® enzyme, which can be filtered by exposing the hits to known concentrations of NanoLuc® enzyme and removing leads that attenuate the NanoLuc® luciferase signal directly.

Cross-Screen Toxicity and Teratogenicity—Therapeutic Index

To prioritize compounds as potential leads for testing in mammalian models a 'therapeutic index' (TI) is calculated for each confirmed hit. For our purposes, TI is calculated as the ratio between the 50% lethal concentration (LC50) and the minimal effective concentration (LC50/ECmin). Compounds with the highest TI ratios are prioritized as lead candidates and further delineated using assays to assess effects teratogenic effects.

Identify Mechanism of Action and Perform Secondary Screens for Metabolic Benefits An advantage of the JHDL library is that it is well characterized with regard to targeted signaling pathways. Testing other available small molecule modulators of hit-implicated pathways serves to verify or invalidate specific mechanisms of action in the regulation of ApoB. Additionally, a screen for synergistic combinatorial effects between lead compounds has the potential to greatly increase therapeutic potential over any individual compound.

It is also valuable to evaluate the secondary effects of ApoB-lowering on related metabolic phenotypes. The general approach is to assess the ability of lead compounds to attenuate genetic and dietary-induced metabolic abnormalities using previously developed disease models and fluorescent reporters for insulin signaling, atherosclerotic plaque formation, lipid transport, and inflammation. These high-content secondary screens relies on the VAST automated imaging platform that automatically collects, orients, and images anesthetized zebrafish using a microfluidics array and pattern-matching software. High-content screening with the VAST bioimager is capable of imaging thousands of larvae per week, thus providing ample throughput capacity to function as a secondary screen to HTS.

An additional secondary screen to assess changes in the LDL size distribution relies on gel-based assays rather than high-content imaging. This PAGE protocol above does not require any special instrumentation or expertise, and could easily achieve throughput capacity in excess of 100 samples per day.

Target Identification

Pathway Analysis:

The validated hits from the primary and secondary screening efforts have well-characterized drug targets. Pathway analysis points to common pathways shared between drugs that may have distinct direct targets, but converge on the same downstream effector pathway.

Validation of Pathways and Drug Targets:

The set of predicted targets generated by pathway analysis are validated through treatment with additional compounds known to target the predicted pathway. If the effects of treatment with the additional compounds are similar to those of treatment with the lead compound, it serves as strong evidence that the predicted pathway is the true drug target resulting in the change in ApoB levels.

Combinatorial Screen

Lead compounds are used in combination at each of their respective maximum-effect concentrations and assayed for effectiveness in the primary screening assay. Combinations showing synergistic effects are included as an additional combination therapy for secondary screening.

Secondary Screens for Related Metabolic Phenotypes

Dietary and Genetic Disease Models:

The zebrafish is a powerful established model of metabolic disease. Feeding zebrafish a high-fat diet has been shown to induce obesity and atherosclerotic plaques, and genetic models of diabetes and inflammation have already been developed.

Drug Treatment:

Fish of the appropriate transgenic line are treated continuously from 5 to 12 dpf with the drug concentration that achieved the maximal effect size in the primary screen.

Automated Bioimaging:

Following each of the experimental treatments outlined below as secondary screens, larvae are automatically collected and imaged using the VAST bioimaging platform (see WWW dot UNION BIO dot COM slash VAST slash).

Figure 5A:
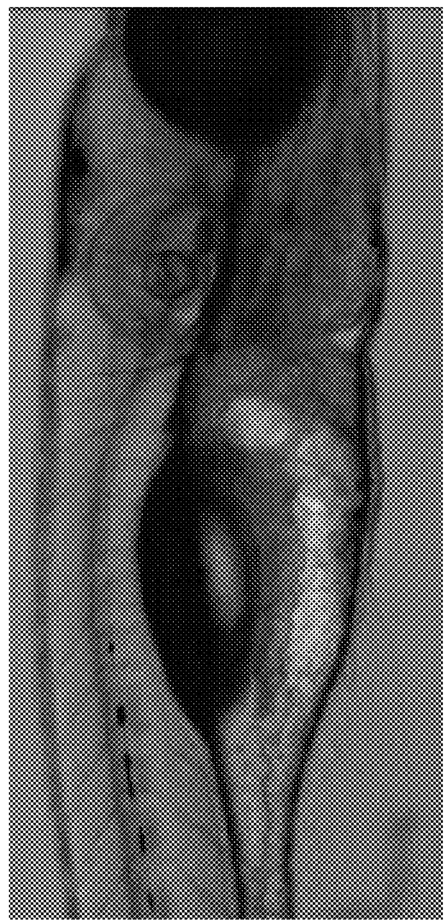
FIGS. 5A and 5B illustrate visualization of fluorescent lipid transport in larvae treated with (FIG. 5A) vehicle control and (FIG. 5B) lomitapide.
Figure 5B:
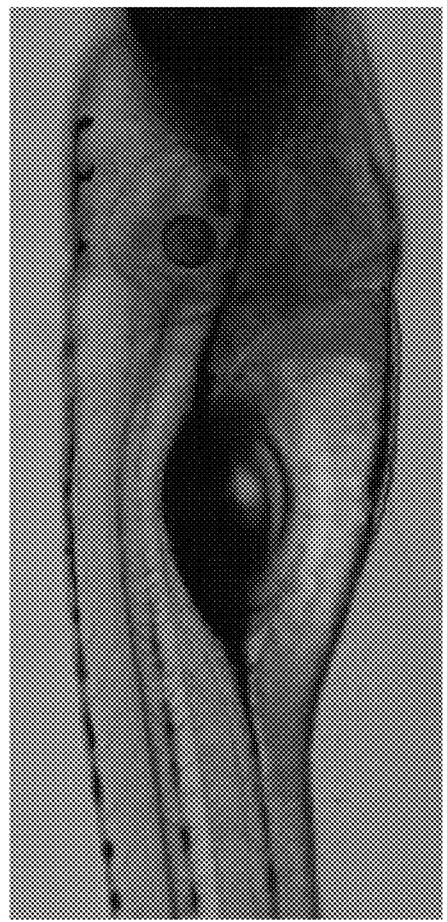

Unbiased Statistical Image Analysis:

We have pioneered "Finotyper"—a statistical analysis pipeline specifically designed to analyze fluorescent images of zebrafish. The program uses principal component analysis to cluster images into statistically significant groups based on the intensity and distribution of fluorescent signal, which can be used to test for differences between control and treatment groups in the high-content secondary imaging screens (FIGS. 5A-5B). Additionally, the program highlights the regions of the image that are responsible for the differential clustering, facilitating identification of the regions effected by treatment.

Secondary Screen for Changes in Lipid Transport

Figure 5C:
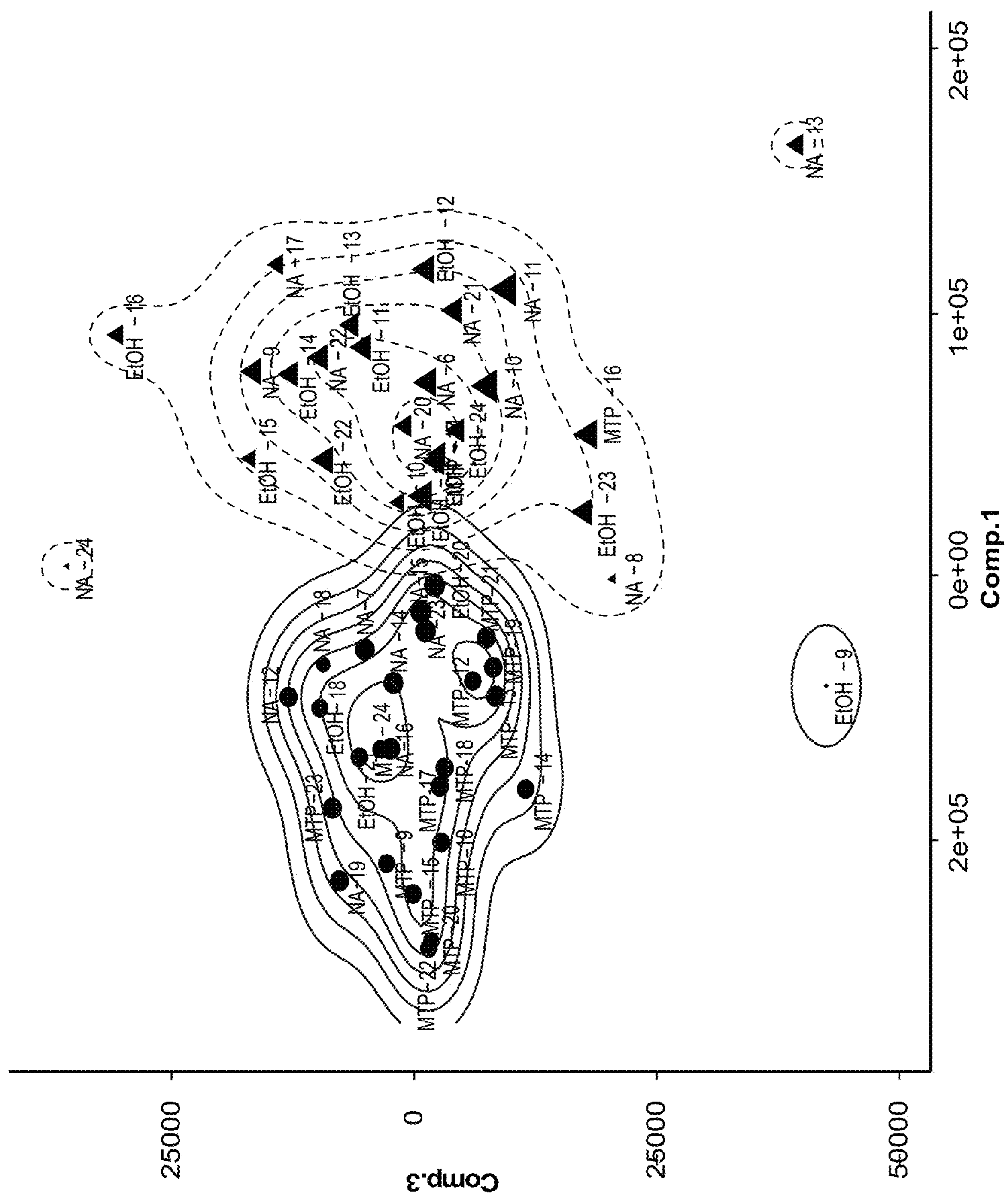
FIG. 5C shows PCA analysis using the finotyper program to separate lomitapide treated (dashed) from vehicle treated controls (solid).

Fluorescent lipid analogs introduced into the diet are absorbed and processed very similarly to natural lipids, and provide a fluorescent readout of lipid accumulation in various tissues. Lipids are absorbed by the intestine and secreted into the bloodstream where they are absorbed by diverse peripheral tissues but accumulate primarily in the liver and gallbladder. A single fluorescent lipid pulse is included in the meal of wild-type larval zebrafish pretreated with lead compounds of interest or vehicle control. Following termination of the feed and a 4-hour chase period, fluorescent lipid localization is recorded by the VAST bioimager and analyzed for differences in treatment groups using finotyper (FIG. 5C).

Secondary Screen for Changes in Insulin Signaling

Phosphoenolpyruvate carboxylase (pepck) is a hepatic enzyme essential for gluconeogenesis, and is therefore upregulated in the fasting state as well as states of insulin resistance. A fluorescent and bioluminescent reporter of phosphoenolpyruvate carboxykinase (pck1) has already been developed as a means of screening for compounds that improve insulin signaling in larval zebrafish. Changes in reporter gene expression following drug treatment are collected and analyzed with the VAST-Finotyper pipeline.

Secondary Screen for Changes in Atherogenesis

Zebrafish is an established model of atherogenic plaque formation with multiple approaches to assess plaque formation in vivo. One approach involves feeding of fluorescent lipid analogs, which have been shown to accumulate in perivascular punctae in response to high-fat diet. Additionally, a transgenic zebrafish line has been developed that expresses a fluorescent antibody to oxidized LDL on an inducible heat-shock promoter (hsp-70:scaOxLDL). High fat feeding promotes formation of plaques rich in oxidized LDL that can be visualized following acute heat shock. Assessment of lead compounds for atheroprotective effects in the context of high-fat diet can be useful in prioritizing hits for clinical development, and correlation of these data with lipoprotein size distribution provides further insight into the relationship between LDL size distribution and atherogenic potential. Changes in antibody localization are assessed using the VAST-Finotyper pipeline.

Secondary Screen for Changes in Inflammation

Transgenic reporters of inflammation have also been developed for the larval zebrafish. Generation of hydrogen peroxide is a hallmark of inflammation, and the HyPer sensor relays the increase in hydrogen peroxide production into a fluorescent readout through fusion of a modified yellow fluorescent protein (cpYFP) to a split version of the prokaryotic hydrogen peroxide sensing protein OxyR. Ratiometric measurement of the native and cross-linked fluorescent signals from the HyPer sensor provides a localized readout of inflammation. The HyPer sensor fish are exposed to a high fat diet including treatment with lead compounds of interest or carrier control and assessed for changes in the degree of inflammation induced as well as the tissue localization using the VAST-Finotyper pipeline.

Secondary Screen for Changes in Lipoprotein Size Distribution

Figure 6A:
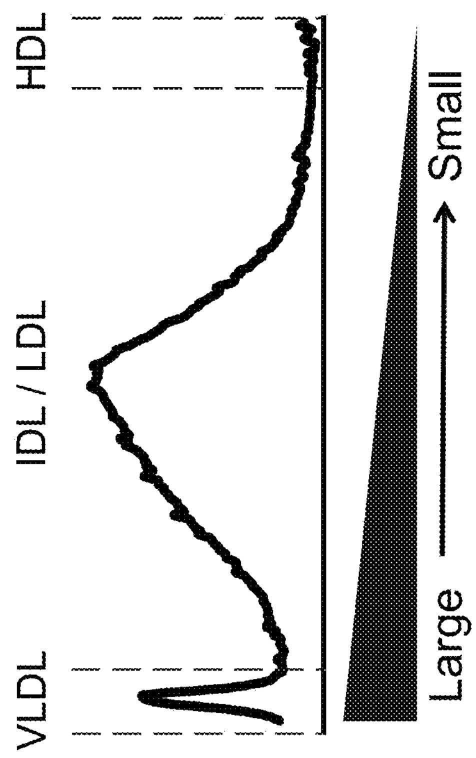
FIGS. 6A and 6B show LDL-size distributions in (FIG. 6A) normal in untreated controls but (FIG. 6B) particle size and number are greatly reduced in the lomitapide-treated sample.
Figure 6B:
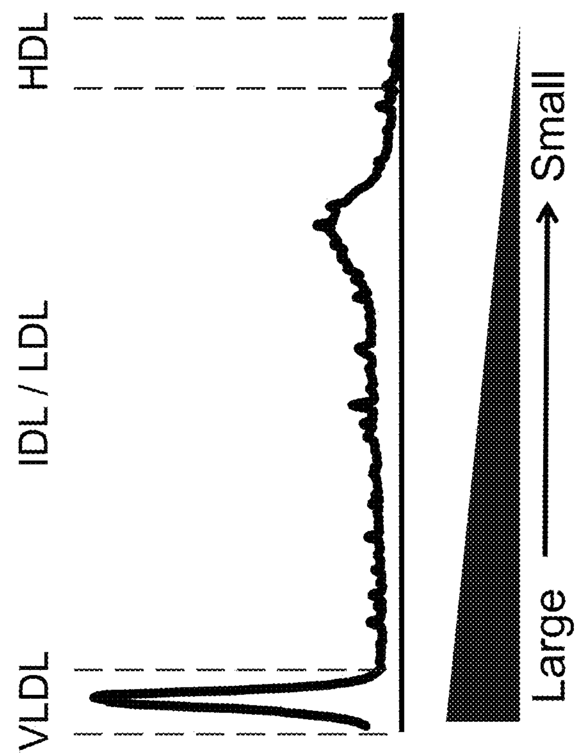

The size distribution of atherogenic lipoprotein particles is a potentially important risk factor for CVD, as smaller LDL particles have been shown to have numerous atherogenic properties, including resistance to clearance by the LDL-receptor, higher propensity to enter the vascular intima, and higher susceptibility to oxidation. The in-gel luciferase assay developed in our lab provides the opportunity to rapidly and sensitively detect changes in lipoprotein size distribution using individual larval zebrafish. Following a week of high-fat diet with or without treatment of test compound, larval zebrafish are homogenized and lipoproteins are separated on a 3% native PAGE gel and imaged using the in-gel luciferase reporter. This enables rapid assessment of lead compounds on effects of the potentially clinically important lipoprotein size distribution phenotype. As a proof of principle, this method was used to assess the change in lipoprotein size distribution in response to acute lomitapide treatment (FIGS. 6A-6B). Lomitapide treatment caused a significant reduction in ApoB levels, and also induced the formation of very small lipoprotein particles.

The present invention has developed a high-throughput phenotypic screen for modulators of ApoB in larval zebrafish and presents a remarkable opportunity to perform unbiased investigation of drug targets in every cell and tissue type while compensating for all the complex signaling and feedback typical of vertebrate metabolism, thus maximizing the likelihood of identifying viable pre-therapeutic leads. This approach can have a resounding impact on the burden of metabolic disease by providing numerous resources to the research and clinical communities, including: (1) an in vivo HTS assay for modulators of ApoB, (2) identification of novel genetic regulators of ApoB, (3) a collection of probes for studying the regulation of ApoB, (4) improved methods for automated image analysis, (5) extensive characterization of relationships between ApoB and related metabolic disease abnormalities, and (6) promising pre-therapeutic leads for treatment of several metabolic diseases.

Apolipoprotein-B (ApoB) is a remarkable biomarker for metabolic health, as it integrates many of the central risk factors for metabolic disease into a single phenotypic readout. Insulin resistance and hepatic triglyceride accumulation both increase ApoB levels, and elevated ApoB in turn promotes ER stress, atherogenesis, and chronic inflammation. ApoB levels are consequently one of the strongest predictors of diabetes, metabolic syndrome, and cardiovascular disease in humans. Compounds that lower ApoB levels could therefore engender numerous metabolic benefits, including improvement of insulin sensitivity, reduction of hepatic triglyceride content, uncoupling of metabolic dysfunction from diabetes and cardiovascular disease risk, amelioration of ER-stress and chronic inflammation, or some combination of these actions. In order to identify such compounds, an in vivo, high-throughput screen (HTS) for ApoB-lowering compounds using transgenic zebrafish larvae carrying an optical reporter of ApoB is carried out.

The larval zebrafish is ideal for our study as it (i) recapitulates all major aspects of vertebrate metabolism in a small, rapidly developing organism, (ii) is the only vertebrate system conducive to HTS, and (iii) has a proven to be a powerful model for drug discovery owing to remarkably conserved physiology and pharmacology with humans. We have used state-of-the-art genome engineering techniques to create transgenic zebrafish carrying a luciferase reporter fused to ApoB (ApoB-NanoLuc® luciferase), which enable rapid, accurate, and highly sensitive quantification of ApoB levels at high-throughput rates using an automated whole-organism screening platform developed for zebrafish chemical biology assays. The primary screen uses the published Automated Reporter Quantification in vivo coupled to High-Throughput Screening (ARQiv-HTS) to identify novel modulators of ApoB in live zebrafish using the ApoB-NanoLuc® luciferase reporter. The assay is a titration-based, in vivo, phenotypic screen that includes an internal counterscreen, secondary validation, and orthogonal screening, thus encompassing many of the best practices in the field and maximizing the probability of success. A pilot screen is performed using a ~3,000 compound library, and post hoc statistics and subsampling is used to optimize the layout and screen an additional 30,000 compounds.

ApoB is an Underappreciated Therapeutic Target for Treatment of Metabolic Disease Pharmaceutical treatments for metabolic disease have historically focused on regulating serum metabolite levels, such as normalizing glucose levels in the context of diabetes and lowering serum cholesterol levels to prevent cardiovascular disease. However, these treatments allow many intracellular and systemic metabolic abnormalities to persist. ApoB is both a useful biomarker and a causative agent for many of the untreated aspects of metabolic disease, and is therefore uniquely powerful therapeutic target, yet drug development efforts have made little progress in this area. Here, we focus on ApoB as a risk factor and use an unbiased in vivo drug discovery approach enabling the identification of compounds that treat the causal factors underlying metabolic disease rather than simply restore serum metabolite homeostasis.

Larval Zebrafish Enable Unbiased In Vivo Screening

ApoB is regulated by a complex homeostatic network involving nutritive, transcriptional, hormonal, and cell-signaling inputs from numerous cell types across almost every major organ. Previous screening efforts in cell culture (1) have been restricted to screening for modulators of ApoB production or uptake in a single cell type, and therefore cannot recapitulate the many intravascular processing, metabolite, endocrine, and neuronal factors contributing to ApoB regulation in vivo. Screening in live vertebrates affords the opportunity for completely unbiased screening that is sensitive to ApoB modulators in every cell and tissue type, but screening in mammalian systems has very limited throughput capacity. The larval zebrafish has recently emerged as the premiere model system for HTS in vivo, as it is easy to produce a large number of rapidly developing organisms that can be maintained and exposed to test compounds in 96-well plate format. Importantly, phenotypic screens such as ours have had remarkably high success rates in first-in-class compound discovery in recent decades (2).

Larval Zebrafish Recapitulate all Major Aspects of ApoB Homeostasis

Larval zebrafish show remarkable conservation of pathways related to ApoB metabolism compared to humans, further justifying their use in our screen. By 5 days post-fertilization, zebrafish larvae have developed all major digestive organs, and therefore possess all the cell and tissue types that contribute to ApoB regulation. The Farber lab has pioneered the use of zebrafish to study apolipoprotein biology (3), and shown that although there are multiple duplications of the ApoB gene in zebrafish, a single isoform (ApoBb.1) is responsible for producing over 95% of the ApoB mRNA and protein from both the liver and intestine. We focus on this single (dominant) isoform. The ApoB coding sequence is well conserved when compared to humans (4, 5), with particularly high sequence conservation in all the essential functional domains such as the MTP-interacting domain, the LDL-receptor binding site, a proline-rich region, and the conserved residue that causes familial hypercholesterolemia when mutated in humans (5-7). Although two of the proline-rich repeats are absent in zebrafish ApoB, these domains are of unknown function and are thought to have arisen from partial gene-duplication and likely have little functional importance (7). In humans, a full-length ApoB-100 protein is expressed in the liver (ApoB-100), but the transcript is post-transcriptionally modified in the intestine to form a truncated (ApoB-48) isoform. Zebrafish have neither the cytosine deaminase enzyme (APOBEC1) nor the conserved modification site (cytosine 6,666) that mediate post-transcriptional processing in mammals (8), indicating that zebrafish produce exclusively full-length (ApoB-100-like) ApoB. The physiological relevance of the truncated ApoB-48 is not well defined, but has been suggested to permit more efficient production of triglyceride-rich lipoproteins under conditions of excess fat intake (9). Importantly, as beta-lipoproteins of both liver (apoB-100) and intestinal (ApoB-48) origin are risk factors for cardiometabolic disease (10), the lack of a truncated isoform in zebrafish allows us to tag all ApoB proteins with a single carboxy-terminal tag. This single reporter fusion protein is therefore sensitive to modulators of both gut and liver derived beta-lipoproteins, and is not susceptible to off-target effects of deamination inhibitors that might confound results in other systems. In addition to high conservation of the functional domains of ApoB, zebrafish also have conserved orthologs of the majority of genes involved in ApoB production, processing, and uptake, and mutations in these genes recapitulate the phenotypes seen in corresponding human disease (11, 12).

Zebrafish Drug Screening is a Powerful Tool for Human Drug Discovery

Zebrafish are not only amenable to high-throughput screening, but compounds discovered in zebrafish have identified promising leads for the development of human drugs. Several drugs discovered in zebrafish screens are in various stages of clinical development, including Prohema (phase II) (13), COX inhibitors (Phase I) (14), Dexamethasone (Phase I) (15), Dorsomorphin (preclinical development) (16), and PROTO-1 (lead optimization) (17). While no drugs initially discovered in zebrafish are yet on the market, this is attributable to the relative infancy of drug screening in zebrafish (over 95% of published zebrafish drug screens took place after 2007) (18) and the long process from drug discovery to market (averaging about 12 years) (19). There are also plentiful examples of human therapeutics showing similar activity in zebrafish, including anti-diabetic, cardiovascular, anti-angiogenic, anti-cancer (20), cardiotoxic, atheroprotective (21), and psychoactive compounds (22, 23). Additionally, zebrafish are highly genetically conserved to humans as 82% of the proteins implicated in human disease have annotated orthologs in zebrafish (24). The high genetic and pharmacological conservation between humans and zebrafish and the success of previous screening efforts provide strong justification for the continued use of zebrafish as a tool for human drug discovery.

Luciferase-Tagged ApoB Permits Sensitive Characterization of Lipoprotein Phenotypes To sensitively detect ApoB-levels in individual zebrafish, we have used TALEN-mediated precise genome engineering to introduce the NanoLuc® luciferase reporter as a carboxy-terminal tag on ApoB. NanoLuc® luciferase is an engineered luciferase reporter that is half the size (14 kDa) and ~100-fold brighter than firefly luciferase, shows essentially no background signal, and allows for independent parallel quantification of a second reporter (firefly luciferase) using a dual-luciferase assay, thus engendering unparalleled sensitivity to our reporter assays (25). We have collected substantial preliminary data to validate that the NanoLuc® luciferase tag does not disrupt ApoB function. We demonstrated that NanoLuc® luciferase signal accumulates in the expected lipoprotein density fractions, that the lipoproteins present in each fraction are the expected sizes (20-60 nm), and that the particles show the expected electrophoretic mobility on a 3% polyacrylamide gel.

We then set out to verify that specific dietary, genetic, and pharmacological manipulations known to modulate ApoB in humans had similar effects in zebrafish. Specifically, a high-fat meal increases lipid availability and concomitantly raises ApoB levels in humans, and the ApoB-NanoLuc® luciferase reporter shows the expected induction in response to high-fat feeding. Humans lacking Apolipoprotein-CII (ApoC2) have profoundly increased ApoB levels (hyperlipoproteinemia type IB) as a result of defects in processing and turnover of ApoB-containing lipoproteins. We have used CRISPR to target the apoc2 gene in zebrafish, and shown that zebrafish show the expected hallmarks of hyperlipoproteinemia type IB including elevated ApoB levels and accumulation of large lipoprotein particles. Finally, pharmaceutical treatment using lomitapide (an MTP inhibitor) results in significant reduction of ApoB levels in humans, and significantly lowered ApoB-NanoLuc® luciferase levels in transgenic larvae as would be expected. Finally, we performed a developmental time-course to determine the optimal treatment window for compound screening. Larvae are nourished by maternal yolk at this stage, which is absorbed and packaged into beta-lipoproteins at a stereotypic rate throughout development and provides predictable reference levels to identify modulators of ApoB A treatment window from 3-5 dpf was selected as the liver is fully differentiated and ApoB is being actively produced and turned over at these stages. In conclusion, in every respect the ApoB-NanoLuc® luciferase reporter has behaved as expected based on our understanding of ApoB biology in humans.

Overview

There are detailed protocols for the development and execution of a high-throughput screen using live vertebrate zebrafish (26, 27). The high-throughput screen uses transgenic zebrafish that carry both an engineered luciferase reporter (NanoLuc® luciferase) fused to ApoB which serves as the primary readout, and a second ubiquitously expressed firefly luciferase reporter that is used as an internal control. Transgenic larvae are raised to 3 days post-fertilization (dpf) and automatically sorted and dispensed into 96-well plates containing various dilutions of test compound. Following 48-hour incubation with test and control compounds, the zebrafish are homogenized and assayed sequentially for Firefly and NanoLuc® luciferase signal using the automated robotics platform and plate reader. Hit-calling software is used to select putative hits, which are validated through repetition and orthogonal screening. The first iteration of the screen uses a modest-sized library (3,000 compounds), and empirical determination of the optimal sample size and number of titration points required for screening enables an increase in throughput for the following iteration of the screen, which screens a 30,000 compound library.

High-Throughput Screening Platform

The primary screen uses the ARQiv-HTS screening platform (automated reporter quantification in vivo coupled to high-throughput screening robotics) (27) to identify compounds that modulate ApoB levels in live zebrafish using the ApoB-NanoLuc® luciferase reporter line. The screening platform is slightly adapted to quantify chemiluminescent (rather than fluorescent) reporters by including a homogenization step and the addition of luciferase substrates.

Reporter Assay Performance

Figure 7:
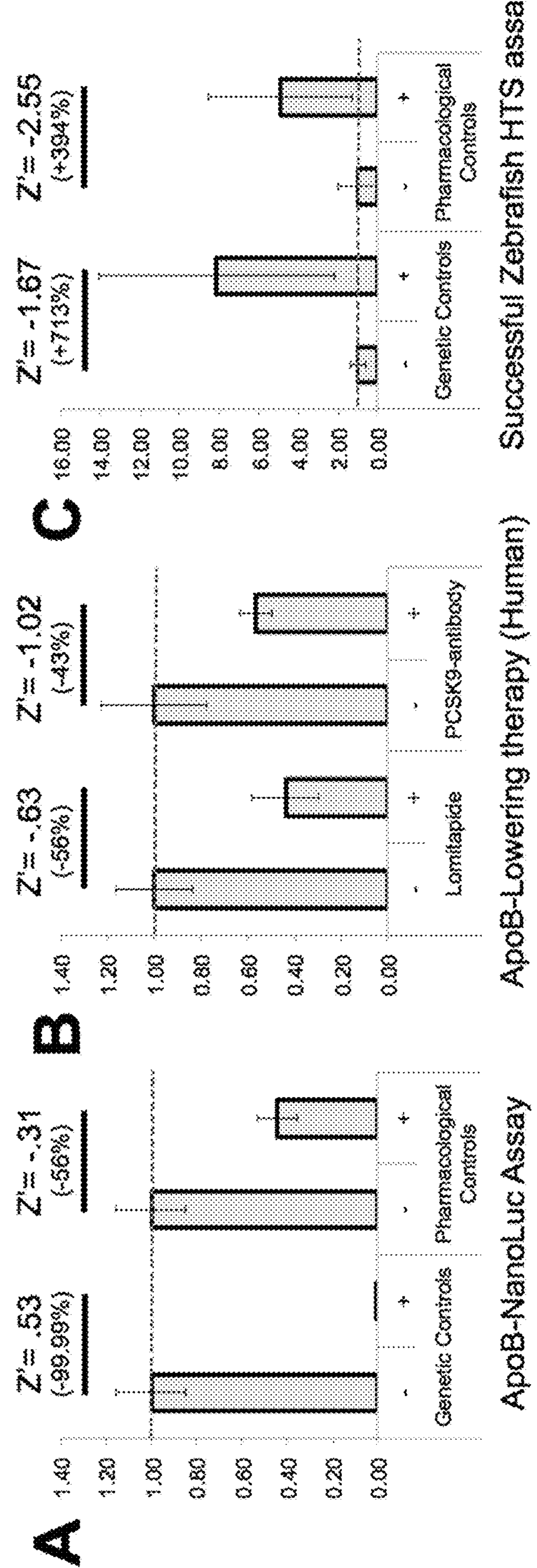
FIGS. 7A to 7C show ApoB-NanoLuc® luciferase reporter assay performance.

Chemiluminescent reporters offer a highly sensitive, quantitative signal with unparalleled signal to noise ratios, making them ideal for HTS applications. This assay uses the transgenic line homozygous for the ApoB-NanoLuc® luciferase reporter described above as a primary readout of ApoB levels. A standard metric for HTS assay quality is the Z'-factor (Z'), which has an arbitrary threshold of 0.5 for an HTS-ready assay (28). Z' calculations for this assay reveal its excellent performance (>0.5) based on genetic positive and negative controls (FIG. 7A, reflecting very high signal to background ratios), but poorer performance based on lomitapide, the best pharmacological positive control available (FIG. 7A). Poorer assay performance in the latter experiment is a result of both the inherent variability of live vertebrate systems, as well as the lack of availability of a sufficiently potent ApoB-lowering therapy to use as a positive control. To contextualize these calculations, humans treated with the strongest ApoB-lowering therapies available (lomitapide and a PCSK9 antibody) show similar magnitudes of reduction in ApoB with higher levels of variability (29, 30) (FIG. 7B), and have poorer Z'-factors (−0.63 and −1.02). The lower variability in the zebrafish model is likely due to the highly consistent diet of maternal yolk used to nourish zebrafish during the screen. The inability of the strongest pharmaceuticals available to achieve a Z' greater than 0.5 in humans or zebrafish indicates that this may not be a realistic threshold to screen for modulators of ApoB in live vertebrates.

A previous HTS in live zebrafish was also unable to reach the Z' threshold of 0.5 (FIG. 7C, note screen was for compounds that increase signal), but adopted an alternative statistical framework based on the strictly standardized mean difference (SSMD) statistic, which (i) is frequently used for in vivo screening (such as RNAi-screens), (ii) accounts for the inherent variability in live vertebrate systems, and (iii) is better suited to assays where an extremely strong positive control is not available or appropriate (31, 32). This screen was able to successfully identify over 200 hits from a library of 3,000 compounds, thus providing precedent that the SSMD calculations are a reasonable substitute for the Z'-factor for in vivo HTS (26). The assay described here greatly outperforms the assay used in the previously published screen in zebrafish mentioned above (26) as measured by both the Z'-factor and power calculations.

In summary, the screening assay shows excellent statistical performance based on genetic controls (Z'>0.5), better performance than expected using pharmaceutical controls as compared to ApoB-lowering treatments in humans, and also shows superior assay quality to the previous successful HTS in zebrafish, suggesting a high probability of success in the primary screen.

Sample Size, Error Rate, and Hit Selection Calculations

Statistical resampling of positive control treatments can be used to estimate the appropriate sample size for HTS assays given type I and type II error rate thresholds and a desired cutoff for effect size (27). Assuming a type II error rate of 0.01 and setting the hit selection cutoff to 50% the magnitude of positive control treatment generates a log-linear relationship between sample size and type I error rate. A sample size of 9 corresponding to an error rate of 0.01, suggesting that a relatively small number of biological replicates can be used to perform a robust primary screen (previous assays required a sample size of 16). Besides serving as a metric for assay quality, the SSMD score can also be used to determine hit cutoff criteria. This statistical test compares the averages between the negative control and each experimental sample, and then adjusts this difference based on the median absolute deviation (MAD) of each sample, such that samples with high variability are penalized and produce a poor SSMD score even if there is a large difference between the means. In positive control treatments, lomitapide produced an SSMD score of −4.5, reflecting a very strong control assay. The scaling factor formula can be used to determine the SSMD cutoff based on the desired magnitude relative to the positive control. A compound with a 50% effect size relative to MTP was chosen as a physiologically relevant effect size, which would produce an SSMD score of −2.7.

Pilot Screening Protocol

Plate Layout:

The plate layout is similar to that in the ARQiv-HTS protocol (27), in that a positive and negative control plate precedes each block of 10 experimental plates, which are used to ensure that no position effects occur in the screening process as well as collect positive and negative control values for SSMD calculation that temporally bracket the experimental samples and account for signal variation across time. Additionally, each plate includes eight positive and eight negative control samples to account for variability between plates. Test compounds are arrayed in a set of 16 biological replicates and a 5-point titration series of 2-fold dilutions to generate a very high quality data set in the pilot screen. It should be noted that while power calculations suggest that nine biological replicates would be sufficient to detect the desired effect size, nine replicates at five concentrations still occupies more than half of the available wells, precluding screening of two compounds per plate. By choosing to generate a high-quality dataset (with 16 biological replicates) in the pilot screen (one compound per plate), it is possible to optimize the plate layout for the subsequent larger screen and detect compounds with small effect sizes with low error rates. The large-scale screen adopts a different plate layout as suggested by subsampling analysis, with the goal of screening of 2-4 compounds per plate.

Library Selection:

The Johns Hopkins Drug Library (JHDL) is comprised of 3,040 compounds, the majority of which are approved for human use and have characterized molecular mechanism(s) of action (26, 33). This library offers several advantages for the pilot screen; first it maximizes likelihood of identifying positive hits from a relatively small compound library as it is validated against all major drug-target classes. Second, the characterized targets permit rapid identification of putative drug targets through pathway analysis. Lastly, hits from this screen can progress rapidly through clinical trials as they are already approved for human use (34-36). The subsequent large-scale screen uses the 30,000 compound CombiSet library (Chembridge) to maximize diversity within an achievable library size.

Internal Control Dual Luciferase Assay:

The NanoLuc® luciferase reporter uses a different substrate than firefly luciferase, allowing a second luciferase reporter to be measured in parallel as an internal control. We chose to use a transgenic line expressing Firefly luciferase (Fluc) reporter in every cell (driven by the ubiquitin promoter) for this purpose (37). By monitoring levels of firefly luciferase, the screening assay is able to detect if any treatments result in developmental delay, cytotoxicity/death, or general disruptions in transcription, translation, or protein turnover/stability. The internal control line was bred with the ApoB-NanoLuc® luciferase reporter line, and the progeny were incrossed and to create a true-breeding stock homozygous for both reporters.

Screening Protocol:

The protocol has been designed such that up to two simultaneous iterations for the screening protocol can be performed per week.

Day 1: Embryo production and collection—zebrafish homozygous for the ApoB-NanoLuc® luciferase and ubi:Fluc reporters are induced to spawn using custom mass-breeding chambers. Eggs are collected hourly from 9 AM to 2 PM. Embryos are maintained in petri dishes at a density of 5 fish/mL of embryo medium (E3).

Day 2: Raising embryos—Embryos are maintained in E3 (1 dpf).

Day 3: Raising embryos and preparing drug plates—Embryos are maintained in embryo medium (2 dpf). The titration protocol is initiated that dilutes and arrays drugs into 96-well barcoded flat-bottom skirted plates following the plate layout using the Solo automated pippettor. Each well contains 100 μL of E3 with twice the final concentration of compound and vehicle specified in the plate layout. Subsequent dispensing of the zebrafish larvae dilutes this stock to the final treatment concentration.

Day 4: Treatment initiation—The COPAS begins automatically dispensing larval zebrafish into individual wells of each 96 well plate at 3 dpf. Filled plates are lidded and transferred to the housing racks for incubation.

Day 5: Incubation—Larvae continue incubation with test compounds.

Day 6: Quantification—Larvae are transferred to the continuously operating plate-horn sonicator using the plate crane and processed, and 40 μL of the homogenate is transferred to a read plate and quantified for firefly and NanoLuc® luciferase signal in the Tecan M1000 plate reader by serial addition of their respective substrates.

Preliminary Screening Data

We have validated the screening assay protocol on a small collection of compounds implicated in the regulation of lipid and lipoprotein metabolism (FIG. 8A). Consistent with our understanding that very few known compounds modulate ApoB metabolism, none of the compounds tested resulted in a significant change in ApoB except for the positive control compound, lomitapide. The screening assay includes firefly luciferase as an internal control reporter to detect off target or cytotoxic effects, and the majority of compounds tested resulted in almost no effect on firefly luciferase levels, as evidenced by the tight distribution of SSMD scores for firefly luciferase around zero. Cutoff values for firefly luciferase were set to positive (increase in signal) and negative (decrease in signal) 2.4, corresponding to 6 standard deviations away from the average SSMD score. Any SSMD scores outside of this range (denoted by dashed gray lines) is discarded due to off-target effects. Several concentrations of test compounds were lethal to zebrafish larvae, and as expected returned very strong negative SSMD scores (<−10) that clearly signal for exclusion from analysis.

ApoB-NanoLuc® luciferase is the primary readout and the hit selection cutoff is set to −2.7 (FIG. 8B, dashed). Positive control treatment with lomitapide resulted in a dose-dependent decrease in NanoLuc® luciferase levels that exceeds threshold cutoff requirements without affecting the internal control reporter (FIG. 8B).

Results from the preliminary screen support that (i) the screening process is robust and free of false positives, (ii) cytotoxic/lethal compounds can be readily detected and discarded, and (iii) the positive control treatment results in strong, dose-responsive effects that meet all hit selection criteria.

Hit Validation and Orthogonal Screening

Hits identified are re-tested using the primary screen procedure except that compounds producing maximal effects at the periphery of the dilution series are re-titrated to center the effective concentration within the dilution series. Consistently significant results indicates confirmed hits and all others are discarded. Small molecule inhibitors of NanoLuc® enzyme activity serve as a potential source of false-positives, which are filtered out by treating known concentrations of NanoLuc® enzyme with hits from the screen and removing leads that attenuate NanoLuc® luciferase signal directly. A sandwich-ELISA based method specific for fish beta-lipoproteins (MyBioSource, MBS008940) serve as an orthogonal test to validate that hits attenuate ApoB levels using a measurement method independent of the NanoLuc® luciferase reporter.

Empirical Optimization of Plate Layout and Execution of Optimized Large-Scale Screen The pilot screen is performed using a sample size of 16 biological replicates across a 5-point titration series of 2-fold dilutions, as power calculations suggest that this produces a very high-quality dataset. This dataset is used to empirically determine the effects of sample size and number of titration points on error rates by repeatedly sampling subsets of the data (bootstrapping). An optimized screen is then executed using the refined plate layout that optimizes throughput capacity while keeping error rates low based on empirical data. This optimized screen can execute two iterations of the screen per week, and is projected to run approximately twice as long (~2 years), permitting a four-fold increase in library size without modification of the plate layout. If the layout can be modified to include 2-4 drugs per plate, this results in an 8-16 fold increase in overall throughput capacity. The CombiSet library (Chembridge) is ideal for our screen as it maximizes library diversity within a manageable library size (30,000 compounds).

Figure 9:
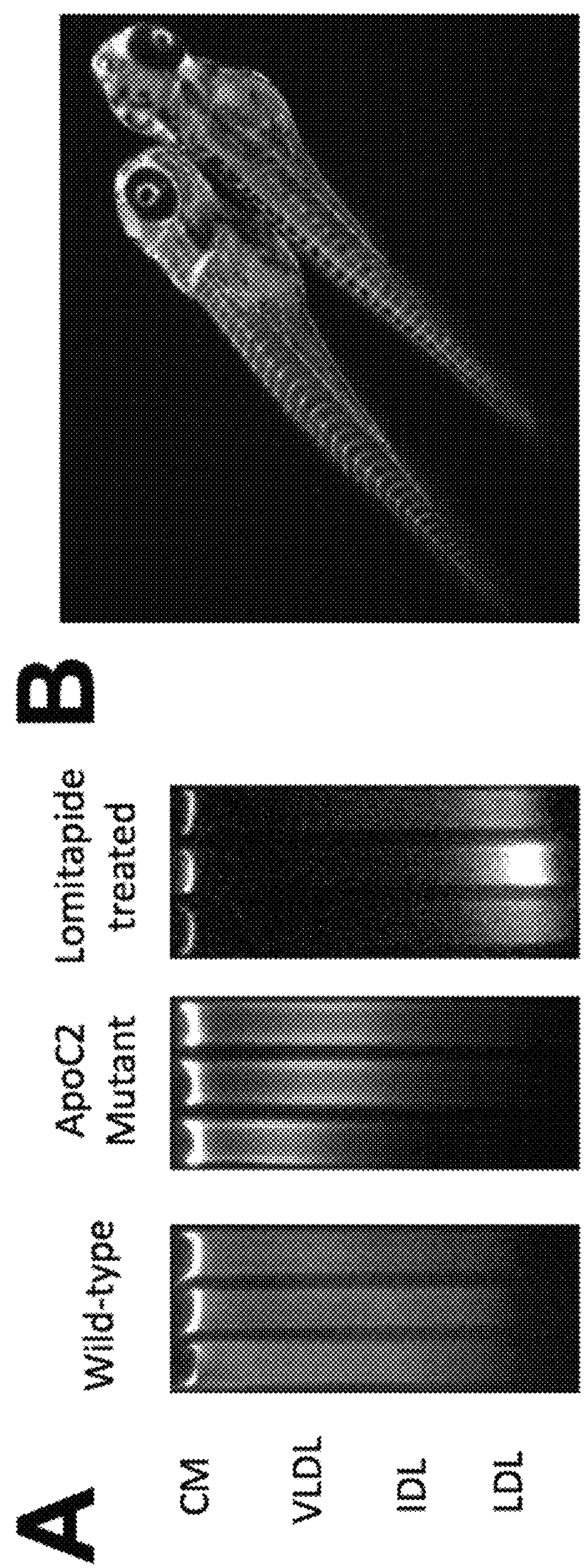
FIGS. 9A and 9B show the size distribution and localization of ApoB-containing particles.

Additional Assays to Characterize the Size and Localization of ApoB-Containing Particles In addition to its utility as a high-throughput compatible readout for measuring levels of Apolipoprotein B, the described ApoB-NanoLuc® luciferase reporter can also be used to measure the size distribution and localization of ApoB-containing particles in zebrafish larvae. Lipoproteins separated using polyacrylamide gel electrophoresis can be sensitively detected in individual larval homogenates by immersing the gel in the NanoLuc® luciferase substrate. The gel shown confirms that, as expected, fish lacking the ApoC2 gene are unable to lipolyze large lipoprotein particles: chylomicrons (CM) and very-low density lipoprotein (VLDL) particles into their smaller counterparts, intermediate density lipoproteins (IDL) and low-density lipoproteins (LDL) (FIG. 9A). Conversely, fish treated with the MTP inhibitor lomitapide are unable to create large lipoprotein particles (FIG. 9A). Additionally, immersion of transgenic larvae in the luciferase substrate enables visualization of the localization of ApoB throughout the organism (FIG. 9B).

The pilot screen is performed using a sample size of 16 biological replicates across a 5-point titration series of 2-fold dilutions, as power calculations suggest that this produces a very high-quality dataset. This dataset is used to empirically determine the effects of sample size and number of titration points on error rates by repeatedly sampling subsets of the data (bootstrapping). An optimized screen is then executed using the refined plate layout that optimizes throughput capacity while keeping error rates low based on empirical data. This optimized screen can execute two iterations of the screen per week, and is projected to run approximately twice as long (~2 years), permitting a four-fold increase in library size without modification of the plate layout. If the layout can be modified to include 2-4 drugs per plate, this results in an 8-16 fold increase in overall throughput capacity. The CombiSet library (Chembridge) is ideal for our screen as it maximizes library diversity within a manageable library size (30,000 compounds).

REFERENCES

1. Kraehling et al. Genome-wide RNAi screen reveals ALK1 mediates LDL uptake and transcytosis in endothelial cells. Nat. Comm. 7:13516, 2016.
2. Swinney & Anthony. How were new medicines discovered? Nature Rev. Drug Discovery 10:507-519, 2011.
3. Otis et al. Zebrafish as a model for apolipoprotein biology: Comprehensive expression analysis and a role for ApoA-IV in regulating food intake. Dis. Model Mech. 8:295-309, 2015.
4. Babin et al. Both apolipoprotein E and A-I genes are present in a nonmammalian vertebrate and are highly expressed during embryonic development. Proc. Natl. Acad. Sci. USA 94:8622-8627, 1997.
5. Koch et al. Detection of the apolipoprotein B-100 Arg (3500)>gl mutation in familial defective apoB-100 by temperature-gradient gel electrophoresis. Z. Gastroenterol. 34 Suppl 3:16-18, 1996.
6. De Loof et al. Human apolipoprotein B: analysis of internal repeats and homology with other apolipoproteins. J. Lipid Res. 28:1455-1465, 1987.
7. Segrest et al. apoB-100 has a pentapartite structure composed of three amphipathic alpha-helical domains alternating with two amphipathic beta-strand domains. Detection by the computer program LOCATE. Arterioscler. Thromb. 14:1674-1685, 1994.
8. Davidson & Shelness. Apolipoprotein B: mRNA editing, lipoprotein assembly, and presecretory degradation. Ann. Rev. Nutr. 20:169-193, 2000.
9. Lo et al. Why does the gut choose apolipoprotein B48 but not B100 for chylomicron formation? Am. J. Physiol. Gastrointest. Liver Physiol. 294:G344-G352, 2008.
10. Alaupovic et al. The role of triglyceride-rich lipoprotein families in the progression of atherosclerotic lesions as determined by sequential coronary angiography from a controlled clinical trial. Arterioscler. Thromb. Vasc. Biol. 17:715-722, 1997.
11. Liu et al. Apoc2 loss-of-function zebrafish mutant as a genetic model of hyperlipidemia. Dis. Model Mech. 8:989-998, 2015.
12. Zu et al. TALEN-mediated precise genome modification by homologous recombination in zebrafish. Nat. Methods 10:329-331, 2013.
13. North et al. Prostaglandin E2 regulates vertebrate haematopoietic stem cell homeostasis. Nature 447:1007-1011, 2007.
14. Yeh et al. Discovering chemical modifiers of oncogene-regulated hematopoietic differentiation. Nat. Chem. Biol. 5:236-243, 2009.
15. Peal et al. Novel chemical suppressors of long QT syndrome identified by an in vivo functional screen. Circulation 123:23-30, 2011.
16. Yu et al. Dorsomorphin inhibits BMP signals required for embryogenesis and iron metabolism. Nat. Chem. Biol. 4:33-41, 2008.
17. Owens et al. Identification of genetic and chemical modulators of zebrafish mechanosensory hair cell death. PLoS Genet. 4:e1000020, 2008.
18. MacRae & Peterson. Zebrafish as tools for drug discovery. Nat. Rev. Drug Discov. 14:721-731, 2015.
19. DiMasi et al. Innovation in the pharmaceutical industry: New estimates of R&D costs. J. Health Econ. 47:20-33, 2016.
20. Langheinrich. Zebrafish: A new model on the pharmaceutical catwalk. Bioessays 25:904-912, 2003.
21. Fang et al. In vivo visualization and attenuation of oxidized lipid accumulation in hypercholesterolemic zebrafish. J. Clin. Invest. 121:4861-4869, 2011.
22. Rihel et al. Zebrafish behavioral profiling links drugs to biological targets and rest/wake regulation. Science 327: 348-351, 2010.
23. Winter et al. Validation of a larval zebrafish locomotor assay for assessing the seizure liability of early-stage development drugs. J. Pharmacol. Toxicol. Methods 57:176-187, 2008.
24. Howe et al. The zebrafish reference genome sequence and its relationship to the human genome. Nature 496: 498-503, 2013.
25. Stacer et al. NanoLuc reporter for dual luciferase imaging in living animals. Mol. Imaging 12:1-13, 2013.
26. Wang et al. First quantitative high-throughput screen in zebrafish identifies novel pathways for increasing pancreatic beta-cell mass. Elife 4:e08261, 2015.
27. White et al. ARQiv-HTS, a versatile whole-organism screening platform enabling in vivo drug discovery at high-throughput rates. Nat. Protoc. 11:2432-2453, 2016.
28. Zhang et al. A simple statistical parameter for use in evaluation and validation of high throughput screening assays. J. Biomol. Screen. 4:67-73, 1999.
29. Sullivan et al. Effect of a monoclonal antibody to PCSK9 on low-density lipoprotein cholesterol levels in statin-intolerant patients: The GAUSS randomized trial. J. Am. Med. Asooc. 308:2497-2506, 2012.
30. Cuchel et al. Inhibition of microsomal triglyceride transfer protein in familial hypercholesterolemia. New Engl. J. Med. 356:148-156, 2007.
31. Zhang. Illustration of SSMD, z score, SSMD*, z* score, and t statistic for hit selection in RNAi high-throughput screens. J. Biomol. Screen. 16:775-785, 2011.
32. Zhang. Novel analytic criteria and effective plate designs for quality control in genome-scale RNAi screens. J. Biomol. Screen. 13:363-377, 2008.
33. Shim & Liu. Recent advances in drug repositioning for the discovery of new anticancer drugs. Intl. J. Biol. Sci. 10:654-663, 2014.
34. Abbott. Neurologists strike gold in drug screen effort. Nature 417:109, 2002.
35. Rothstein et al. Beta-lactam antibiotics offer neuroprotection by increasing glutamate transporter expression. Nature 433:73-77, 2005.
36. Stavrovskaya et al. Clinically approved heterocyclics act on a mitochondrial target and reduce stroke-induced pathology. J. Exp. Med. 200:211-222, 2004.
37. Chen et al. Zebraflash transgenic lines for in vivo bioluminescence imaging of stem cells and regeneration in adult zebrafish. Development 140:4988-4997, 2013.

All references cited herein are hereby incorporated by reference to the same extent as if each reference were individually and specifically indicated to be incorporated by reference and were set forth in its entirety herein.

A term such as “a” or “an” or “the” in the context of describing the invention (especially in the context of the claims) is to be construed as including both the singular (“one”) and the plural (“more than one”), unless otherwise indicated herein or clearly contradicted by context. The terms “comprising,” “having,” “including,” and “containing” are to be construed as open-ended terms (i.e., meaning “including, but not limited to”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The examples and exemplary language (e.g., "such as") provided herein, are intended merely to better understand the invention and are not limitations on the scope of the invention unless the exemplified element is recited in the claim. No language in the specification should be construed as indicating that a non-claimed element is essential to the practice of the invention.

Specific embodiments are described herein, including the best mode known to the inventors for carrying out the invention. Variations of those specific embodiments may become apparent to a person skilled in the art upon reading the foregoing description. Thus, one of skill in the art could practice the invention using such variations as appropriate, and the inventors intend for the invention to be practiced otherwise than as specifically described herein. Accordingly, this description includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for high-throughput, in vivo screening; the method comprising:

(a) applying an agent to a zebrafish expressing an Apolipoprotein B (ApoB)-reporter fusion protein;

(b) monitoring the reporter activity;

(c) comparing the reporter activity to a second reporter activity of a reference; and (d) identifying a modulator of ApoB.

2. The method according to claim 1, wherein the ApoB-reporter fusion protein is expressed from an ApoBb.1 locus-reporter gene.

3. The method according to claim 1, wherein the reporter is a luciferase.

4. The method according to claim 1, wherein identifying a modulator of ApoB enhancing ApoB expression occurs when the reporter activity is greater than the second reporter activity of the reference.

5. The method according to claim 1, wherein identifying a modulator of ApoB inhibiting expression of ApoB occurs when the reporter activity is less than the second reporter activity of the reference.

6. The method according to claim 1, wherein the agent is a chemical.

7. The method according to claim 1, wherein the reporter is a luciferase and the ApoB-reporter fusion protein is expressed from a DNA sequence of SEQ ID NO: 3.

8. The method according to claim 1, wherein the ApoB-reporter fusion protein has a protein sequence of SEQ ID NO: 2.

9. A zebrafish comprising an ApoBb.1 locus-reporter fusion gene.

10. The zebrafish as in claim 9, wherein the ApoBb.1 locus-reporter fusion gene has a DNA sequence of SEQ ID NO: 3.

11. The zebrafish as in claim 9 further comprising a genomic ubiquitous promoter driving expression of a firefly luciferase gene.

12. The zebrafish as in claim 9 further comprising a genomic mCherry fluorescent reporter.

13. A method for high-throughput, in vivo screening to identify a modulator of ApoB; the method comprising:

(a) applying agents to zebrafish larvae expressing an ApoB-reporter fusion protein gene and a second reporter protein;

(b) monitoring the ApoB-reporter fusion protein activity and the second reporter protein activity; and (c) comparing the reporter activities to the third reporter activities of a reference.

14. The method according to claim 13, wherein the ApoB-reporter fusion protein is an ApoB-luciferase fusion protein.

15. The method according to claim 14, wherein the ApoB-mutant luciferase fusion protein is expressed from an ApoBb.1 locus-mutant luciferase gene fusion.

16. The method according to claim 13, wherein the monitoring comprises sonicating the zebrafish larvae and then measuring the ApoB-fusion protein activity and the second reporter protein activity by a high content screening (HCS) microscopy platform.

17. The method according to claim 13, wherein the second reporter is firefly luciferase.

* * * * *

SEQUENCE LISTING

<160> NUMBER OF SEQ ID NOS: 3

<210> SEQ ID NO 1
<211> LENGTH: 11733
<212> TYPE: DNA
<213> ORGANISM: Artificial Sequence
<220> FEATURE:
<223> OTHER INFORMATION: ApoBb.1-NanoLuc luciferase nucleotide sequence

<400> SEQUENCE: 1
atggggggga ctaagctctg ccttttgcta cttctatgtg caattgcctt gtcattggcc 60
aaaaggttca agagctttca gaagtatgaa tacacctacg aaacggagtc tctaaatgcc 120
ctgaatggag caatcaatgg tcccaaggcc agatgcaagg ttgaaattga ggtcccacgc 180
atatgcagct atatcgttca cacaactgag tgtgagttga gtgatgtcat cgatgttgat 240
gctgaaggaa agcctatctt tatgtcatct gctggtgcag aggctttcaa ggctgccatg 300
gcaaagaacc ccctgaagtt caccgttgag ggagataatg acatcaagtt gtttcctgag 360
aatgatgaac cagccaacat tttgaacttc aaaagaggtc taatctcagc ccttgcagca 420
cctgtgctgg aggaagacag aaacaggaga atgcccaccg tctacggcat gtgcaggaca 480
gactactctg tgaatgccag acaggatatt gccaccgatg ttgtcctcaa cagagacttg 540
tctaactgtg acaaattcag cccagtcaaa gaccacacta gtcccctggc acttatcaca 600
ggaatgcaat acccacttgc tcagctcatc agaagcagcc aaacctgcaa ctacaagttt 660
gacaatgatc aaaagcatat gacctcggct tcttgctctg aaaaacacat gcttttgcca 720
ttttcttaca aggagagca tggcgtttct aatgtaggaa agcaagcttt gactctggtg 780
ggagtgtctg tatacaacgg cagaatcttt gaccacaatg aagccaacat gaagaccctg 840
catcttgatg acagcattga ctcagtccat ccaattcaag acaaagatgc aatcctgtca 900
attctaaggg acctgaatga cctttctgag accacaaatg gagaaaatag agcccatctt 960
gctcacaaac tcatttctac catccgcaaa atgagtgcag aaagcctgag tgctgctctg 1020
ccagaggcac tggagatttc tcgcccccctt gtgtaccaag ctttgttcca gtgtggcact 1080
cctgaatgca ccagtgccat cctgcgggtt ctcagaacct ttgaccgttc ctctgtagag 1140
attgatgctg cagtgtatgc catgggaatg gttccaaatc catccagaga ccttgttgag 1200
gagatgctgg agatggccaa gttcaaatct agcaagccca tctactatgc tctcagcaat 1260
gctgtgaaga ggctctatga agttgaaaaa agtgtcaccc ctgagatcaa ggcagtcgca 1320
gattacaccc ttgaacagat tggcgactgc acagggaacc aagaacatgt gtacctgtcc 1380
ctgagggtca ttggaaacat ggctgctgct gtcggagctg caagccctgc tctgaaatca 1440
gcagttatcc agtgcataaa ccaacccgct gcatcccctg aggtccagca agctgctatt 1500

-continued

```
caagtattta ggctaacttc tgttcctgac gagggcagag aggtgctaat gaaggtcatt   1560
ttcgacaaag ctgctccaat acagaagcgt gttgctgcgt atctcattgt gatgaaggac   1620
cctcagccca ctgaactggc tcagctggtt gcagctctgc ctaataataa aaactgccag   1680
gctatgagct ttgttaactc acatctccgg aacatcctga gctctacaac atcagagacc   1740
ggggaactca gagtaaagat tcttaatgcc ctgcaaggaa atgagatcag tacttccacc   1800
gatccaacaa aattctctcg caattacaag attggctctc tagagggaaa tgtgattttt   1860
gagtctgaag aacttctgcc caatgaagtc atcctggaga tgaccctaaa tgcctttgga   1920
tatgatgttg acatgtttga gattgggtta aacggaaagg gtctggaacc cactgttgat   1980
gccctgattg gtattgatgg attcttccgt gacaccatgc agaagaccat taactatgca   2040
gctgacaaag taccaagggg caatgacatt atgcagagca tgttcccaac cctatggaat   2100
aacatcaaaa tgcaaaaggc ccctcaaagc attgtcaaag aaataacaaa taatgttaac   2160
aagctcatcc agaagctgaa ggttcaggac aacccagagg ctatgatcta cctgaggctt   2220
ttgggtgctg aaatgggcta tctcaaaact aatgatgtag aagacatggc ctactctgct   2280
gccttgctga ctaaaagcct cctaaatatg ttccctactg atttcctaag gaacctatac   2340
tcaagtgtca acaacaacct tttccttcac tacgtcttca tggacaatga gttttatcta   2400
ccaactggta ccggcattcc tctaagagtt gccctgtctg gtacttttgc tcctggagtg   2460
aagggaggac tgaaacttgc tcgtgacatg agcgaagtgg ctttcatgcc atccgctgga   2520
gttgagtttg tgacggaggt tggagctctc ctacctgaat atgttgagtc tggcctggag   2580
atgcatacta acatctacca cgagagtggt ctcaaagtaa aagttgcagt gaccaataag   2640
cagttcaagt tgaccattcc cacaccaaaa acttcaacaa aactcatcag tgtctcaaac   2700
tcattgtatt cagtgactgg tacagaaatc aagaggattc ctccactggc agagcatgtg   2760
aaagcaagga agtgcactcc tttcattcct ggttttcagt actgcggtgt catgcaatat   2820
tctaatgcct tttccaacga tgccgctccc tacttccctt tgactggtga tagcaaattt   2880
gccattgaga tccacccgac tggtgaggtt tcttcataca cagcaactgc tgattatgca   2940
tatgatggca aagatgacac agtgacattt ggtctgaagg cagaaggaat aacatttgag   3000
agcatagtca aactaacatt cgacagacag aattatgaag tctcggctga cgtccaaatt   3060
cctgactatg acctggaagc tggaattcgg gttcatgctg ttgatcgaaa agctcagagt   3120
gatgccacac attccatcca gattgacttg atgaagaaga atgtacctga agcatctctc   3180
attggtcttg ctaagattgg gtcaatgaag gatgccatgc tgcaggttca gctgctcatt   3240
ccaaattttg agactgatgc taaagtaacg gcaacactaa aaaatactga tgaacttaaa   3300
gtggaacttg aaagtgacat aaagcttcct gagatgacct cctctattca gaaaatgatt   3360
ctgaaatatg atgctgagga aattgaggct gaggtctctt ctgatgtcac cactgagatt   3420
cacaacatta taactactga tgccatcaaa gccacattca atgatattct tgaccaagaa   3480
attggcacat ctgataagaa gatccgtgat gtcttgaccc aatttgttga ggcttcaaat   3540
gcctacctgg agcaattttc tcccaacatt ccatatgtac aggaattgag gattcctgct   3600
ctcccagaat tcactttccc taagaagctg ttcctgaatg ctgagggtgc tgctaaatac   3660
aagtttggcc agaattatta caccataacc atacctgttc ctcttggtgg aaaaacttca   3720
agagatttca acctccctgc tgctctggaa acaccagtac tgaacgtacc acagcttgac   3780
cttcaggtta aatccattaa tatcccactt ccagtgttct ttataccaga gagtctgtct   3840
ctgtcactac ctcttgtggc aaaggcggag gtgtccagca agctgagcag caacttctat   3900
```

```
gacatggaag caaaagcttc tgcagggagt gaacttgtag ataaaccaac ctattctgcc   3960
atgattgaag tcacaggaac aagtccagtg gatctactct ccttcaaaat agaaggatca   4020
accttcctgg taggtagact tggagaatct ttgaagactg agatgaaatc ctcccttaat   4080
cacaagctcc ttgaagccag tgtcaattat tttgaggaaa taacaactgg agaaaaaatc   4140
acaatgaaat caagcagcaa gatggaggcg aaaagtccct ttggtctgaa gatttctctg   4200
gaacacacgg gccaggttgg actcgatgaa gatgagatct ctggagatgg aaatctgttg   4260
ggctctatca aggctggtcc tttgaatggt gaagttgctc tcagacaatc acttatcctt   4320
cttccattca agccagagct gaaaatcgac tcttctctga aagtagactt agaacaaatc   4380
caagcagaga acataattga agcagctttt gccaatggag agctctcttt cacatctaaa   4440
tcaacagcat tccaggacaa tctcatacat gttgctgaac ttgcctataa agaatcacag   4500
cttgctctga agtcagatgc aagggcaaag gctttcggcc taaacatcca aaatgtagct   4560
gaggctagtg ctagttttaa tttagttaac gttaagattg acactaatgt tgacactttg   4620
tttggaaatc gtgtccgttc ccagtttata gcagcactgg acgccaatgg gctggatgta   4680
aaaagtgatg cctctgcaaa tctggatgaa cacacagctt ctcacatgtg cagcctttcc   4740
ctgaccagaa acggcctagt cacaattggc tcaaccttac tagagtgccc agacatgcct   4800
ttgacactgc agaacaaatt caatggagcc cttgacactt cagggctttc attgtcagtt   4860
gaaacaaaag gtaaattcgt tgaagtgaca attgaaaaca caaattctct gtctgcctcc   4920
ctgtcctcag tagatttcat ttccaaagct aatagcgatg atggaacata tgtgcatgac   4980
ttctcccttc agcttcagcc atatagtacc tcgttgaaaa ttagcaataa tctgaatgct   5040
ctgaacatca aactgattaa tgaggcacag tttaaggcac ttccatatgc agcagatctg   5100
actggcagtt ggaagctttc ctctggaaca gatgagctta agaacacata tgagatcaaa   5160
tatgaagatc tggttgctac agccaagtgt ggtctcactg gaaaactcat gggatctcac   5220
atgagccaaa acacagaaat tgaagttgct ggactttcag ttacatacgg cagtgaatcc   5280
aatttcaact cacagtatct ccgcttcaat agcgacttac atgccgctgc tgttcccttc   5340
agattcaacg ttgatgcaat ggtcaatgca gatggggatt tgtatctgta tggaaaacaa   5400
agcgcacaag tctactctaa attccttatg aaggcagaac cacttgcttt tgcacactca   5460
catgaatgca gagtctcaac aacttacaac ctgtatgatg atctggtatt cgaaaccaac   5520
cttgataata aaattgatac tgtgctgaca ccgtctgagc aaaaggccac agtgagagta   5580
aaatctaagt tcaacaacca tgagtttaac aaagacttga gtgcttacaa taccccctgaa   5640
agacttggag ttgaaatgtc tggatccatc atcaccaaca tcttcaatac agttgactct   5700
gacaatcaag accacttttt ctctgccttc ctaaaatatg ataaaaacag caacagccgt   5760
gccttaagtc tgccatttat tgatgagttt ccatttgacc tgcaacacat gaaacttgca   5820
gttttgagga ttgttgaggc catgcagagt tatatcaaca gagaagaaat cattgtagaa   5880
attcagaaac tggccacata tgttagtgac tttgtgaatg aactgaatct ggaagagaaa   5940
atcataaaat tcagcaagga cctgactgcg ctgtatgagg actatggaat tactctcgac   6000
gacctggagg cttctctgat gaatctaaag cctgttttgt tgaagctagt cactgaactt   6060
gacacttatg tagtagagat agaaaagatt gtgagggaaa taattacaag tggcacacca   6120
tctgatgctg caatacagag gtttacagat atcctgaatt cattcaatga gaaatatgac   6180
gtcaaagcca ttgttctcac tgttattgag gctattgaaa aatttcttag ggaaatcgat   6240
gtaatgagta taaagggcag cagggaagtc ttcaagcaat atgttgatga atattttgct   6300
```

```
attaaatcca aagtggagga aattttgagt gaactgaagc agtttgttgc aaactttgac   6360
caagaaaagt tcactgagga tgtgaagaac tttgttacct cagccagatt cagagactat   6420
gcagacaatc tggtggctaa aatcccaaca gagcaaatca gcaagattct tgaaaaagca   6480
aaacaactgc ttaatctact gggtaacaga atgaatgcca tctatacaaa tgtgagagaa   6540
attctggtga aatctggggt tgacaagaag atcgaaactc tcctcaaaaa agttgttgag   6600
cttatcaaga agttcaacat tgaagaaact gttaagactc ttgcggacac tttgaaatct   6660
attctgaccc ctgtcactga gctggtggat aaggccatca actacttgaa aacaacagag   6720
gcaaaggaaa tcattgaaga tctgaacaac tgcctaaacc actgcattaa atatattaga   6780
tcatttgact acaacgcatt tgtggatgag gccaatcaga aaatcaagaa gttaacaaat   6840
gatctttaca ccatgagttt gtcacttgaa atccgtcaaa agcttgaggc aatcagagag   6900
tttgttaact atgctttgtc atctatgagc gcttgcatcg aaaagctgga aaaagtcaaa   6960
gttgtggatg tcgtcaaaaa attcagtgac attgtcgata gtgtagtctt cattgacacc   7020
gaggcactca ttgaggacct taggaaaata cttgcagaca ttgatatcag agaagaaatc   7080
cagaagtttc tgaagcacgc aagtagcatc tccaccaagg ttgtgaccac tgcaacagat   7140
gcatgcagtg ctgttatgca agtgatccaa aacatcctta aagatcaagc agttgtcaac   7200
gagctgaagc aaatctgtga cagagtcaaa acagtactga gaacagctga atttaagatt   7260
ccatctttca tttttccact gactgacctt gttgtgccat ccataaaaat aagcttaaag   7320
aatcttcagg aaatcaacct cccatcttca ctgattgacc ttccagggtt tacaattctg   7380
caatattaca ctgtgccacc aatcagagta gaatatgctg acatcaagca gggactatta   7440
gatctcctgc acttcattgc gaactttgaa ataatgccag ctgtcgagaa catctttggt   7500
gaccttagaa ttgtctacat gcctgacatc tctgccatca cactgccaga gataagctta   7560
ccagagatct ctctcccaga aattcctaaa tacatcagca agcacaaatt ttctgatctg   7620
acaatcccag aattcaccct ccctggagtt cctactgagg tcatggtgcc atgctttgga   7680
aagttgtatg gtgaggttag agtcaccatt ccaattttca acatgagaac tacagtagaa   7740
ttcctaaact ctactgaaag tgcagaaacc cctcagtttg tagggcacat tacctcacat   7800
ggatcttcag aatatgacct tcttaaatac accttggact ccacagctcg tgttgccatg   7860
cctaaaatga gtcgtgtgat tcttgcagaa accctgaaga tcactcacag tgtactagcc   7920
attgaccatc aatcctcagt ctcactttat ggcctctcag cccaggcttc ttccaagagc   7980
accatgaaga ttacctcttc cacctataat gctaacatcg ttaacactgc tttctttgcc   8040
ctggcaggtg gaatatctgc aaatatcaaa acaacatata atgacaagtt aaatgcagac   8100
ctttggaaca gtgaatatta ttacggtaat gatataattc taaagcagga tggtctaaaa   8160
ctccttctga ccatggaaga agaggccaag ggacatatat ctgtgctcga aaagtctgat   8220
gatatcactg gcaagagtag ttcatctata attattactc caacaacatt ctctctgatc   8280
atttctgtgg attccagcag ttctgtttca aacattaaaa aaagtattaa agctgacggt   8340
gttgctctga gctatgtcga cttcactgcc agcattgaag gaactagtga ttctgagtta   8400
tttttactga atgcagctgg aaaggcggat ctcagacaaa tgaaagtaga gatgaaggct   8460
gaccttgaca caaaatatgc tggactgctc agtggtacct tcaccagtgc ctttaacttc   8520
ttagtgcaac cttttgaggt agtccttgat ttcaagaaca aggctaatac taagctcaac   8580
cttgtagagc ccctgtctgc taagattgat cttcagaaca attatactgt catccttaat   8640
agcgacgagc agatgttgag cactgggtta cttgcccgct ttaaccagta caagtacagt   8700
```

-continued

```
cacaatttca cattggccaa caacgaggat gaggctggca tttatgctgc agtaaatggc   8760
gaggctaatt tggaattcct aacaatccct ttcagtattc cagcaatgga attagaaaca   8820
ctaactatgg taattgaaat tccagaaatc agtaacatca atctatatga acagactggg   8880
cttaagcatg ttttgactga cttcgaccag gccattgatg tagatgcaaa gatggtttac   8940
cagaagaatg acttaacctc tgagttgtct ttcaagtcct ccatattcaa tcttaatgcc   9000
aatgctggtt tctatcagaa ggataaccct gtaattcgtt ttggagtcat cactgcttct   9060
gagtttgagt cactgaaggc caagcttgaa ggaaccagca gtctgagcac caaaagtgga   9120
ttcaaattag ccaattcttt gcttctagaa aatcgccaca ttgaaggaac ccatgaaagc   9180
actgcaacta tgaacctgaa taactttgaa gttacactgt ctatggccac agatgcaaaa   9240
atgaatctac caattcttac agctaatgcc aaccaccaac ttactgctga caacaaggcc   9300
aacccaaaag cagactcaac atttaagatg gattacaact ttgacgttcc cattattaag   9360
cttgttggaa agggaaatgc tgaaaccatc ttaaaaggcg aaggaactcg tacgtttatc   9420
tctgctgaga cacttataaa gagcaatatt gatggaacat tcctagatcg tggtattttg   9480
aaaggaactc tgaattacga tgaatccctg tatgtgaatg gtaatagttt gcgatatgcc   9540
cttaagactg gtggtaatgg agacctgaac tatggtgatt tcaaggtggc ttttgatgtg   9600
gatgaaaacc tgtctgtaga gacagccaat gagcacgtat atgctacaat gaagtttact   9660
tccaataatg aagcaaatgt tggatctttc aacactaaag gagttcattc cagccaggct   9720
actctcgata tggctcttct gaagtcactg gtggctgata tgaaaataga cttgtctcaa   9780
ccgagcacct ttggtgaact tagcatcttc gagacaatga aagtagatct cagtgctccc   9840
aagcagaaaa ttgatatcct ttcaacaatc aagtctccgg tatacaccac agatgttcgt   9900
gctaaactag acggtaatgc cccagattac aaaacggttc tgaaggcttc agccacttca   9960
ccagttgtgc gcctgcagta tgatcttgac agctccatga gttctactat ggagaatggt  10020
gcccttgttg tcggagctaa cgctgtactt acacatcagg acttcactat ggatatcagc  10080
aatgctattc gcatgagcga aaggagccat attctgaatg tggacatcac cagccaaaca  10140
tttaccgatg ttaaccttcg ctatgctgct cggagtgatg ggataagtgg ctctgtttcc  10200
acaccggggt ctggcctcct tggctttcag ctccaaggaa atattccatc ccaaatgaat  10260
gcaaggctct actgtcgtta tgcttttgca ccagatgatg atgtcgacat cctaagcgtc  10320
agagccgtac caaagggaga tgaaaaagta ctgttggtca ctggcaatat aaaggctgca  10380
caatccatgt ttgaaggctt aatgaatact ctagaaaaaa tctcatttaa acttgcagga  10440
ttagcaagag aatatggtct cgcttttcca atttttgttg ctgacgatgt ttatggagta  10500
atttcaaatg gactctctgc tgcccgcaga gctacaccag gcgttagtga gttatcccaa  10560
cttttcagaa atgtagttgt cacatcccaa aagaccatcc aggtcttgat tgacaatgcc  10620
atcgtactcg taaaagagat ttcacaatat aaactgcctg gaatgaatga agctacactg  10680
gctgaaattt gcaagaaaat ccaattagtt gttgtagaaa tgctgaggaa ttttggtaac  10740
aacttggagg tatacttctc tcccatcatg gataacttta atacaattca attgacattt  10800
cccaatggaa aggtcatgac agtagctgag ttccaacaaa atgtgcagag tatcctgaga  10860
agcaacctag ttatgatagc agatgcaatg aagcaaatcg aaagtcctga tgtagttctt  10920
aagaaacttg gacaaacttt acaagaggtt gttgaaaaag gacaagagtt tgtggacaaa  10980
atgaatttaa gtttattaga agatattgcc gcggccatta acacgttcta cctggagctc  11040
atgaagatca tagaagacat tagtgaggca gtcatgtttg gtttttcaat ccctgcaatt  11100
```

```
aaaatatatg aaatgtctca aaacatagag aaagtgttga acgcaaataa tggaatacat  11160

caatttgagc ttcctctccc atttttccag acaagtttgt acaaaaaagc aggcttgatg  11220

gtcttcacac tcgaagattt cgttggggac tggcgacaga cagccggcta caacctggac  11280

caagtccttg aacagggagg tgtgtccagt ttgtttcaga atctcggggt gtccgtaact  11340

ccgatccaaa ggattgtcct gagcggtgaa aatgggctga agatcgacat ccatgtcatc  11400

atcccgtatg aaggtctgag cggcgaccaa atgggccaga tcgaaaaaat ttttaaggtg  11460

gtgtaccctg tggatgatca tcactttaag gtgatcctgc actatggcac actggtaatc  11520

gacggggtta cgccgaacat gatcgactat ttcggacggc cgtatgaagg catcgccgtg  11580

ttcgacggca aaaagatcac tgtaacaggg accctgtgga acggcaacaa aattatcgac  11640

gagcgcctga tcaaccccga cggctccctg ctgttccgag taaccatcaa cggagtgacc  11700

ggctggcggc tgtgcgaacg cattctggcg taa                              11733
```

<210> SEQ ID NO 2
<211> LENGTH: 3910
<212> TYPE: PRT
<213> ORGANISM: Artificial Sequence
<220> FEATURE:
<223> OTHER INFORMATION: ApoBb.1-NanoLuc luciferase amino acid sequence

<400> SEQUENCE: 2

```
Met Gly Gly Thr Lys Leu Cys Leu Leu Leu Leu Leu Cys Ala Ile Ala
1               5                   10                  15

Leu Ser Leu Ala Lys Arg Phe Lys Ser Phe Gln Lys Tyr Glu Tyr Thr
            20                  25                  30

Tyr Glu Thr Glu Ser Leu Asn Ala Leu Asn Gly Ala Ile Asn Gly Pro
        35                  40                  45

Lys Ala Arg Cys Lys Val Glu Ile Glu Val Pro Arg Ile Cys Ser Tyr
    50                  55                  60

Ile Val His Thr Thr Glu Cys Glu Leu Ser Asp Val Ile Asp Val Asp
65                  70                  75                  80

Ala Glu Gly Lys Pro Ile Phe Met Ser Ser Ala Gly Ala Glu Ala Phe
                85                  90                  95

Lys Ala Ala Met Ala Lys Asn Pro Leu Lys Phe Thr Val Glu Gly Asp
            100                 105                 110

Asn Asp Ile Lys Leu Phe Pro Glu Asn Asp Glu Pro Ala Asn Ile Leu
        115                 120                 125

Asn Phe Lys Arg Gly Leu Ile Ser Ala Leu Ala Ala Pro Val Leu Glu
    130                 135                 140

Glu Asp Arg Asn Arg Arg Met Pro Thr Val Tyr Gly Met Cys Arg Thr
145                 150                 155                 160

Asp Tyr Ser Val Asn Ala Arg Gln Asp Ile Ala Thr Asp Val Val Leu
                165                 170                 175

Asn Arg Asp Leu Ser Asn Cys Asp Lys Phe Ser Pro Val Lys Asp His
            180                 185                 190

Thr Ser Pro Leu Ala Leu Ile Thr Gly Met Gln Tyr Pro Leu Ala Gln
        195                 200                 205

Leu Ile Arg Ser Ser Gln Thr Cys Asn Tyr Lys Phe Asp Asn Asp Gln
    210                 215                 220

Lys His Met Thr Ser Ala Ser Cys Ser Glu Lys His Met Leu Leu Pro
225                 230                 235                 240

Phe Ser Tyr Lys Gly Glu His Gly Val Ser Asn Val Gly Lys Gln Ala
                245                 250                 255
```

-continued

```
Leu Thr Leu Val Gly Val Ser Val Tyr Asn Gly Arg Ile Phe Asp His
            260                 265                 270

Asn Glu Ala Asn Met Lys Thr Leu His Leu Asp Asp Ser Ile Asp Ser
        275                 280                 285

Val His Pro Ile Gln Asp Lys Asp Ala Ile Leu Ser Ile Leu Arg Asp
    290                 295                 300

Leu Asn Asp Leu Ser Glu Thr Thr Asn Gly Glu Asn Arg Ala His Leu
305                 310                 315                 320

Ala His Lys Leu Ile Ser Thr Ile Arg Lys Met Ser Ala Glu Ser Leu
                325                 330                 335

Ser Ala Ala Leu Pro Glu Ala Leu Glu Ile Ser Arg Pro Leu Val Tyr
            340                 345                 350

Gln Ala Leu Phe Gln Cys Gly Thr Pro Glu Cys Thr Ser Ala Ile Leu
        355                 360                 365

Arg Val Leu Arg Thr Phe Asp Arg Ser Ser Val Glu Ile Asp Ala Ala
    370                 375                 380

Val Tyr Ala Met Gly Met Val Pro Asn Pro Ser Arg Asp Leu Val Glu
385                 390                 395                 400

Glu Met Leu Glu Met Ala Lys Phe Lys Ser Ser Lys Pro Ile Tyr Tyr
                405                 410                 415

Ala Leu Ser Asn Ala Val Lys Arg Leu Tyr Glu Val Glu Lys Ser Val
            420                 425                 430

Thr Pro Glu Ile Lys Ala Val Ala Asp Tyr Thr Leu Glu Gln Ile Gly
        435                 440                 445

Asp Cys Thr Gly Asn Gln Glu His Val Tyr Leu Ser Leu Arg Val Ile
    450                 455                 460

Gly Asn Met Ala Ala Ala Val Gly Ala Ala Ser Pro Ala Leu Lys Ser
465                 470                 475                 480

Ala Val Ile Gln Cys Ile Asn Gln Pro Ala Ala Ser Pro Glu Val Gln
                485                 490                 495

Gln Ala Ala Ile Gln Val Phe Arg Leu Thr Ser Val Pro Asp Glu Gly
            500                 505                 510

Arg Glu Val Leu Met Lys Val Ile Phe Asp Lys Ala Ala Pro Ile Gln
        515                 520                 525

Lys Arg Val Ala Ala Tyr Leu Ile Val Met Lys Asp Pro Gln Pro Thr
    530                 535                 540

Glu Leu Ala Gln Leu Val Ala Ala Leu Pro Asn Asn Lys Asn Cys Gln
545                 550                 555                 560

Ala Met Ser Phe Val Asn Ser His Leu Arg Asn Ile Leu Ser Ser Thr
                565                 570                 575

Thr Ser Glu Thr Gly Glu Leu Arg Val Lys Ile Leu Asn Ala Leu Gln
            580                 585                 590

Gly Asn Glu Ile Ser Thr Ser Thr Asp Pro Thr Lys Phe Ser Arg Asn
        595                 600                 605

Tyr Lys Ile Gly Ser Leu Glu Gly Asn Val Ile Phe Glu Ser Glu Glu
    610                 615                 620

Leu Leu Pro Asn Glu Val Ile Leu Glu Met Thr Leu Asn Ala Phe Gly
625                 630                 635                 640

Tyr Asp Val Asp Met Phe Glu Ile Gly Leu Asn Gly Lys Gly Leu Glu
                645                 650                 655

Pro Thr Val Asp Ala Leu Ile Gly Ile Asp Gly Phe Phe Arg Asp Thr
            660                 665                 670
```

-continued

```
Met Gln Lys Thr Ile Asn Tyr Ala Ala Asp Lys Val Pro Arg Gly Asn
        675                 680                 685

Asp Ile Met Gln Ser Met Phe Pro Thr Leu Trp Asn Asn Ile Lys Met
    690                 695                 700

Gln Lys Ala Pro Gln Ser Ile Val Lys Glu Ile Thr Asn Asn Val Asn
705                 710                 715                 720

Lys Leu Ile Gln Lys Leu Lys Val Gln Asp Asn Pro Glu Ala Met Ile
                725                 730                 735

Tyr Leu Arg Leu Leu Gly Ala Glu Met Gly Tyr Leu Lys Thr Asn Asp
            740                 745                 750

Val Glu Asp Met Ala Tyr Ser Ala Ala Leu Leu Thr Lys Ser Leu Leu
        755                 760                 765

Asn Met Phe Pro Thr Asp Phe Leu Arg Asn Leu Tyr Ser Ser Val Asn
    770                 775                 780

Asn Asn Leu Phe Leu His Tyr Val Phe Met Asp Asn Glu Phe Tyr Leu
785                 790                 795                 800

Pro Thr Gly Thr Gly Ile Pro Leu Arg Val Ala Leu Ser Gly Thr Phe
                805                 810                 815

Ala Pro Gly Val Lys Gly Gly Leu Lys Leu Ala Arg Asp Met Ser Glu
            820                 825                 830

Val Ala Phe Met Pro Ser Ala Gly Val Glu Phe Val Thr Glu Val Gly
        835                 840                 845

Ala Leu Leu Pro Glu Tyr Val Glu Ser Gly Leu Glu Met His Thr Asn
    850                 855                 860

Ile Tyr His Glu Ser Gly Leu Lys Val Lys Val Ala Val Thr Asn Lys
865                 870                 875                 880

Gln Phe Lys Leu Thr Ile Pro Thr Pro Lys Thr Ser Thr Lys Leu Ile
                885                 890                 895

Ser Val Ser Asn Ser Leu Tyr Ser Val Thr Gly Thr Glu Ile Lys Arg
            900                 905                 910

Ile Pro Pro Leu Ala Glu His Val Lys Ala Arg Lys Cys Thr Pro Phe
        915                 920                 925

Ile Pro Gly Phe Gln Tyr Cys Gly Val Met Gln Tyr Ser Asn Ala Phe
    930                 935                 940

Ser Asn Asp Ala Ala Pro Tyr Phe Pro Leu Thr Gly Asp Ser Lys Phe
945                 950                 955                 960

Ala Ile Glu Ile His Pro Thr Gly Glu Val Ser Ser Tyr Thr Ala Thr
                965                 970                 975

Ala Asp Tyr Ala Tyr Asp Gly Lys Asp Asp Thr Val Thr Phe Gly Leu
            980                 985                 990

Lys Ala Glu Gly Ile Thr Phe Glu  Ser Ile Val Lys Leu  Thr Phe Asp
        995                 1000                 1005

Arg Gln  Asn Tyr Glu Val Ser  Ala Asp Val Gln Ile  Pro Asp Tyr
    1010                 1015                 1020

Asp Leu  Glu Ala Gly Ile Arg  Val His Ala Val Asp  Arg Lys Ala
    1025                 1030                 1035

Gln Ser  Asp Ala Thr His Ser  Ile Gln Ile Asp Leu  Met Lys Lys
    1040                 1045                 1050

Asn Val  Pro Glu Ala Ser Leu  Ile Gly Leu Ala Lys  Ile Gly Ser
    1055                 1060                 1065

Met Lys  Asp Ala Met Leu Gln  Val Gln Leu Leu Ile  Pro Asn Phe
    1070                 1075                 1080
```

```
Glu Thr  Asp Ala Lys Val Thr  Ala Thr Leu Lys Asn  Thr Asp Glu
    1085                 1090                 1095

Leu Lys  Val Glu Leu Glu Ser  Asp Ile Lys Leu Pro  Glu Met Thr
    1100                 1105                 1110

Ser Ser  Ile Gln Lys Met Ile  Leu Lys Tyr Asp Ala  Glu Glu Ile
    1115                 1120                 1125

Glu Ala  Glu Val Ser Ser Asp  Val Thr Thr Glu Ile  His Asn Ile
    1130                 1135                 1140

Ile Thr  Thr Asp Ala Ile Lys  Ala Thr Phe Asn Asp  Ile Leu Asp
    1145                 1150                 1155

Gln Glu  Ile Gly Thr Ser Asp  Lys Lys Ile Arg Asp  Val Leu Thr
    1160                 1165                 1170

Gln Phe  Val Glu Ala Ser Asn  Ala Tyr Leu Glu Gln  Phe Ser Pro
    1175                 1180                 1185

Asn Ile  Pro Tyr Val Gln Glu  Leu Arg Ile Pro Ala  Leu Pro Glu
    1190                 1195                 1200

Phe Thr  Phe Pro Lys Lys Leu  Phe Leu Asn Ala Glu  Gly Ala Ala
    1205                 1210                 1215

Lys Tyr  Lys Phe Gly Gln Asn  Tyr Tyr Thr Ile Thr  Ile Pro Val
    1220                 1225                 1230

Pro Leu  Gly Gly Lys Thr Ser  Arg Asp Phe Asn Leu  Pro Ala Ala
    1235                 1240                 1245

Leu Glu  Thr Pro Val Leu Asn  Val Pro Gln Leu Asp  Leu Gln Val
    1250                 1255                 1260

Lys Ser  Ile Asn Ile Pro Leu  Pro Val Phe Phe Ile  Pro Glu Ser
    1265                 1270                 1275

Leu Ser  Leu Ser Leu Pro Leu  Val Ala Lys Ala Glu  Val Ser Ser
    1280                 1285                 1290

Lys Leu  Ser Ser Asn Phe Tyr  Asp Met Glu Ala Lys  Ala Ser Ala
    1295                 1300                 1305

Gly Ser  Glu Leu Val Asp Lys  Pro Thr Tyr Ser Ala  Met Ile Glu
    1310                 1315                 1320

Val Thr  Gly Thr Ser Pro Val  Asp Leu Leu Ser Phe  Lys Ile Glu
    1325                 1330                 1335

Gly Ser  Thr Phe Leu Val Gly  Arg Leu Gly Glu Ser  Leu Lys Thr
    1340                 1345                 1350

Glu Met  Lys Ser Ser Leu Asn  His Lys Leu Leu Glu  Ala Ser Val
    1355                 1360                 1365

Asn Tyr  Phe Glu Glu Ile Thr  Thr Gly Glu Lys Ile  Thr Met Lys
    1370                 1375                 1380

Ser Ser  Ser Lys Met Glu Ala  Lys Ser Pro Phe Gly  Leu Lys Ile
    1385                 1390                 1395

Ser Leu  Glu His Thr Gly Gln  Val Gly Leu Asp Glu  Asp Glu Ile
    1400                 1405                 1410

Ser Gly  Asp Gly Asn Leu Leu  Gly Ser Ile Lys Ala  Gly Pro Leu
    1415                 1420                 1425

Asn Gly  Glu Val Ala Leu Arg  Gln Ser Leu Ile Leu  Leu Pro Phe
    1430                 1435                 1440

Lys Pro  Glu Leu Lys Ile Asp  Ser Ser Leu Lys Val  Asp Leu Glu
    1445                 1450                 1455

Gln Ile  Gln Ala Glu Asn Ile  Ile Glu Ala Ala Phe  Ala Asn Gly
    1460                 1465                 1470
```

-continued

```
Glu Leu Ser Phe Thr Ser Lys Ser Thr Ala Phe Gln Asp Asn Leu
    1475                1480                1485

Ile His Val Ala Glu Leu Ala Tyr Lys Glu Ser Gln Leu Ala Leu
    1490                1495                1500

Lys Ser Asp Ala Arg Ala Lys Ala Phe Gly Leu Asn Ile Gln Asn
    1505                1510                1515

Val Ala Glu Ala Ser Ala Ser Phe Asn Leu Val Asn Val Lys Ile
    1520                1525                1530

Asp Thr Asn Val Asp Thr Leu Phe Gly Asn Arg Val Arg Ser Gln
    1535                1540                1545

Phe Ile Ala Ala Leu Asp Ala Asn Gly Leu Asp Val Lys Ser Asp
    1550                1555                1560

Ala Ser Ala Asn Leu Asp Glu His Thr Ala Ser His Met Cys Ser
    1565                1570                1575

Leu Ser Leu Thr Arg Asn Gly Leu Val Thr Ile Gly Ser Thr Leu
    1580                1585                1590

Leu Glu Cys Pro Asp Met Pro Leu Thr Leu Gln Asn Lys Phe Asn
    1595                1600                1605

Gly Ala Leu Asp Thr Ser Gly Leu Ser Leu Ser Val Glu Thr Lys
    1610                1615                1620

Gly Lys Phe Val Glu Val Thr Ile Glu Asn Thr Asn Ser Leu Ser
    1625                1630                1635

Ala Ser Leu Ser Ser Val Asp Phe Ile Ser Lys Ala Asn Ser Asp
    1640                1645                1650

Asp Gly Thr Tyr Val His Asp Phe Ser Leu Gln Leu Gln Pro Tyr
    1655                1660                1665

Ser Thr Ser Leu Lys Ile Ser Asn Asn Leu Asn Ala Leu Asn Ile
    1670                1675                1680

Lys Leu Ile Asn Glu Ala Gln Phe Lys Ala Leu Pro Tyr Ala Ala
    1685                1690                1695

Asp Leu Thr Gly Ser Trp Lys Leu Ser Ser Gly Thr Asp Glu Leu
    1700                1705                1710

Lys Asn Thr Tyr Glu Ile Lys Tyr Glu Asp Leu Val Ala Thr Ala
    1715                1720                1725

Lys Cys Gly Leu Thr Gly Lys Leu Met Gly Ser His Met Ser Gln
    1730                1735                1740

Asn Thr Glu Ile Glu Val Ala Gly Leu Ser Val Thr Tyr Gly Ser
    1745                1750                1755

Glu Ser Asn Phe Asn Ser Gln Tyr Leu Arg Phe Asn Ser Asp Leu
    1760                1765                1770

His Ala Ala Ala Val Pro Phe Arg Phe Asn Val Asp Ala Met Val
    1775                1780                1785

Asn Ala Asp Gly Asp Leu Tyr Leu Tyr Gly Lys Gln Ser Ala Gln
    1790                1795                1800

Val Tyr Ser Lys Phe Leu Met Lys Ala Glu Pro Leu Ala Phe Ala
    1805                1810                1815

His Ser His Glu Cys Arg Val Ser Thr Thr Tyr Asn Leu Tyr Asp
    1820                1825                1830

Asp Leu Val Phe Glu Thr Asn Leu Asp Asn Lys Ile Asp Thr Val
    1835                1840                1845

Leu Thr Pro Ser Glu Gln Lys Ala Thr Val Arg Val Lys Ser Lys
    1850                1855                1860
```

```
Phe Asn  Asn His Glu Phe Asn  Lys Asp Leu Ser Ala  Tyr Asn Thr
    1865                 1870                 1875

Pro Glu  Arg Leu Gly Val Glu  Met Ser Gly Ser Ile  Ile Thr Asn
    1880                 1885                 1890

Ile Phe  Asn Thr Val Asp Ser  Asp Asn Gln Asp His  Phe Phe Ser
    1895                 1900                 1905

Ala Phe  Leu Lys Tyr Asp Lys  Asn Ser Asn Ser Arg  Ala Leu Ser
    1910                 1915                 1920

Leu Pro  Phe Ile Asp Glu Phe  Pro Phe Asp Leu Gln  His Met Lys
    1925                 1930                 1935

Leu Ala  Val Leu Arg Ile Val  Glu Ala Met Gln Ser  Tyr Ile Asn
    1940                 1945                 1950

Arg Glu  Glu Ile Ile Val Glu  Ile Gln Lys Leu Ala  Thr Tyr Val
    1955                 1960                 1965

Ser Asp  Phe Val Asn Glu Leu  Asn Leu Glu Glu Lys  Ile Ile Lys
    1970                 1975                 1980

Phe Ser  Lys Asp Leu Thr Ala  Leu Tyr Glu Asp Tyr  Gly Ile Thr
    1985                 1990                 1995

Leu Asp  Asp Leu Glu Ala Ser  Leu Met Asn Leu Lys  Pro Val Leu
    2000                 2005                 2010

Leu Lys  Leu Val Thr Glu Leu  Asp Thr Tyr Val Val  Glu Ile Glu
    2015                 2020                 2025

Lys Ile  Val Arg Glu Ile Ile  Thr Ser Gly Thr Pro  Ser Asp Ala
    2030                 2035                 2040

Ala Ile  Gln Arg Phe Thr Asp  Ile Leu Asn Ser Phe  Asn Glu Lys
    2045                 2050                 2055

Tyr Asp  Val Lys Ala Ile Val  Leu Thr Val Ile Glu  Ala Ile Glu
    2060                 2065                 2070

Lys Phe  Leu Arg Glu Ile Asp  Val Met Ser Ile Lys  Gly Ser Arg
    2075                 2080                 2085

Glu Val  Phe Lys Gln Tyr Val  Asp Glu Tyr Phe Ala  Ile Lys Ser
    2090                 2095                 2100

Lys Val  Glu Glu Ile Leu Ser  Glu Leu Lys Gln Phe  Val Ala Asn
    2105                 2110                 2115

Phe Asp  Gln Glu Lys Phe Thr  Glu Asp Val Lys Asn  Phe Val Thr
    2120                 2125                 2130

Ser Ala  Arg Phe Arg Asp Tyr  Ala Asp Asn Leu Val  Ala Lys Ile
    2135                 2140                 2145

Pro Thr  Glu Gln Ile Ser Lys  Ile Leu Glu Lys Ala  Lys Gln Leu
    2150                 2155                 2160

Leu Asn  Leu Leu Gly Asn Arg  Met Asn Ala Ile Tyr  Thr Asn Val
    2165                 2170                 2175

Arg Glu  Ile Leu Val Lys Ser  Gly Val Asp Lys Lys  Ile Glu Thr
    2180                 2185                 2190

Leu Leu  Lys Lys Val Val Glu  Leu Ile Lys Lys Phe  Asn Ile Glu
    2195                 2200                 2205

Glu Thr  Val Lys Thr Leu Ala  Asp Thr Leu Lys Ser  Ile Leu Thr
    2210                 2215                 2220

Pro Val  Thr Glu Leu Val Asp  Lys Ala Ile Asn Tyr  Leu Lys Thr
    2225                 2230                 2235

Thr Glu  Ala Lys Glu Ile Ile  Glu Asp Leu Asn Asn  Cys Leu Asn
    2240                 2245                 2250
```

-continued

```
His Cys  Ile Lys Tyr Ile Arg  Ser Phe Asp Tyr Asn  Ala Phe Val
    2255                 2260                 2265

Asp Glu  Ala Asn Gln Lys Ile  Lys Lys Leu Thr Asn  Asp Leu Tyr
    2270                 2275                 2280

Thr Met  Ser Leu Ser Leu Glu  Ile Arg Gln Lys Leu  Glu Ala Ile
    2285                 2290                 2295

Arg Glu  Phe Val Asn Tyr Ala  Leu Ser Ser Met Ser  Ala Cys Ile
    2300                 2305                 2310

Glu Lys  Leu Glu Lys Val Lys  Val Val Asp Val Val  Lys Lys Phe
    2315                 2320                 2325

Ser Asp  Ile Val Asp Ser Val  Val Phe Ile Asp Thr  Glu Ala Leu
    2330                 2335                 2340

Ile Glu  Asp Leu Arg Lys Ile  Leu Ala Asp Ile Asp  Ile Arg Glu
    2345                 2350                 2355

Glu Ile  Gln Lys Phe Leu Lys  His Ala Ser Ser Ile  Ser Thr Lys
    2360                 2365                 2370

Val Val  Thr Thr Ala Thr Asp  Ala Cys Ser Ala Val  Met Gln Val
    2375                 2380                 2385

Ile Gln  Asn Ile Leu Lys Asp  Gln Ala Val Val Asn  Glu Leu Lys
    2390                 2395                 2400

Gln Ile  Cys Asp Arg Val Lys  Thr Val Leu Arg Thr  Ala Glu Phe
    2405                 2410                 2415

Lys Ile  Pro Ser Phe Ile Phe  Pro Leu Thr Asp Leu  Val Val Pro
    2420                 2425                 2430

Ser Ile  Lys Ile Ser Leu Lys  Asn Leu Gln Glu Ile  Asn Leu Pro
    2435                 2440                 2445

Ser Ser  Leu Ile Asp Leu Pro  Gly Phe Thr Ile Leu  Gln Tyr Tyr
    2450                 2455                 2460

Thr Val  Pro Pro Ile Arg Val  Glu Tyr Ala Asp Ile  Lys Gln Gly
    2465                 2470                 2475

Leu Leu  Asp Leu Leu His Phe  Ile Ala Asn Phe Glu  Ile Met Pro
    2480                 2485                 2490

Ala Val  Glu Asn Ile Phe Gly  Asp Leu Arg Ile Val  Tyr Met Pro
    2495                 2500                 2505

Asp Ile  Ser Ala Ile Thr Leu  Pro Glu Ile Ser Leu  Pro Glu Ile
    2510                 2515                 2520

Ser Leu  Pro Glu Ile Pro Lys  Tyr Ile Ser Lys His  Lys Phe Ser
    2525                 2530                 2535

Asp Leu  Thr Ile Pro Glu Phe  Thr Leu Pro Gly Val  Pro Thr Glu
    2540                 2545                 2550

Val Met  Val Pro Cys Phe Gly  Lys Leu Tyr Gly Glu  Val Arg Val
    2555                 2560                 2565

Thr Ile  Pro Ile Phe Asn Met  Arg Thr Thr Val Glu  Phe Leu Asn
    2570                 2575                 2580

Ser Thr  Glu Ser Ala Glu Thr  Pro Gln Phe Val Gly  His Ile Thr
    2585                 2590                 2595

Ser His  Gly Ser Ser Glu Tyr  Asp Leu Leu Lys Tyr  Thr Leu Asp
    2600                 2605                 2610

Ser Thr  Ala Arg Val Ala Met  Pro Lys Met Ser Arg  Val Ile Leu
    2615                 2620                 2625

Ala Glu  Thr Leu Lys Ile Thr  His Ser Val Leu Ala  Ile Asp His
    2630                 2635                 2640
```

```
Gln Ser  Ser Val Ser Leu Tyr  Gly Leu Ser Ala Gln  Ala Ser Ser
    2645                 2650                 2655

Lys Ser  Thr Met Lys Ile Thr  Ser Ser Thr Tyr Asn  Ala Asn Ile
    2660                 2665                 2670

Val Asn  Thr Ala Phe Phe Ala  Leu Ala Gly Gly Ile  Ser Ala Asn
    2675                 2680                 2685

Ile Lys  Thr Thr Tyr Asn Asp  Lys Leu Asn Ala Asp  Leu Trp Asn
    2690                 2695                 2700

Ser Glu  Tyr Tyr Tyr Gly Asn  Asp Ile Ile Leu Lys  Gln Asp Gly
    2705                 2710                 2715

Leu Lys  Leu Leu Leu Thr Met  Glu Glu Glu Ala Lys  Gly His Ile
    2720                 2725                 2730

Ser Val  Leu Glu Lys Ser Asp  Asp Ile Thr Gly Lys  Ser Ser Ser
    2735                 2740                 2745

Ser Ile  Ile Ile Thr Pro Thr  Thr Phe Ser Leu Ile  Ile Ser Val
    2750                 2755                 2760

Asp Ser  Ser Ser Ser Val Ser  Asn Ile Lys Lys Ser  Ile Lys Ala
    2765                 2770                 2775

Asp Gly  Val Ala Leu Ser Tyr  Val Asp Phe Thr Ala  Ser Ile Glu
    2780                 2785                 2790

Gly Thr  Ser Asp Ser Glu Leu  Phe Leu Leu Asn Ala  Ala Gly Lys
    2795                 2800                 2805

Ala Asp  Leu Arg Gln Met Lys  Val Glu Met Lys Ala  Asp Leu Asp
    2810                 2815                 2820

Thr Lys  Tyr Ala Gly Leu Leu  Ser Gly Thr Phe Thr  Ser Ala Phe
    2825                 2830                 2835

Asn Phe  Leu Val Gln Pro Phe  Glu Val Val Leu Asp  Phe Lys Asn
    2840                 2845                 2850

Lys Ala  Asn Thr Lys Leu Asn  Leu Val Glu Pro Leu  Ser Ala Lys
    2855                 2860                 2865

Ile Asp  Leu Gln Asn Asn Tyr  Thr Val Ile Leu Asn  Ser Asp Glu
    2870                 2875                 2880

Gln Met  Leu Ser Thr Gly Leu  Leu Ala Arg Phe Asn  Gln Tyr Lys
    2885                 2890                 2895

Tyr Ser  His Asn Phe Thr Leu  Ala Asn Asn Glu Asp  Glu Ala Gly
    2900                 2905                 2910

Ile Tyr  Ala Ala Val Asn Gly  Glu Ala Asn Leu Glu  Phe Leu Thr
    2915                 2920                 2925

Ile Pro  Phe Ser Ile Pro Ala  Met Glu Leu Glu Thr  Leu Thr Met
    2930                 2935                 2940

Val Ile  Glu Ile Pro Glu Ile  Ser Asn Ile Asn Leu  Tyr Glu Gln
    2945                 2950                 2955

Thr Gly  Leu Lys His Val Leu  Thr Asp Phe Asp Gln  Ala Ile Asp
    2960                 2965                 2970

Val Asp  Ala Lys Met Val Tyr  Gln Lys Asn Asp Leu  Thr Ser Glu
    2975                 2980                 2985

Leu Ser  Phe Lys Ser Ser Ile  Phe Asn Leu Asn Ala  Asn Ala Gly
    2990                 2995                 3000

Phe Tyr  Gln Lys Asp Asn Pro  Val Ile Arg Phe Gly  Val Ile Thr
    3005                 3010                 3015

Ala Ser  Glu Phe Glu Ser Leu  Lys Ala Lys Leu Glu  Gly Thr Ser
    3020                 3025                 3030
```

```
Ser Leu  Ser Thr Lys Ser Gly  Phe Lys Leu Ala Asn  Ser Leu Leu
    3035                 3040                 3045

Leu Glu  Asn Arg His Ile Glu  Gly Thr His Glu Ser  Thr Ala Thr
    3050                 3055                 3060

Met Asn  Leu Asn Asn Phe Glu  Val Thr Leu Ser Met  Ala Thr Asp
    3065                 3070                 3075

Ala Lys  Met Asn Leu Pro Ile  Leu Thr Ala Asn Ala  Asn His Gln
    3080                 3085                 3090

Leu Thr  Ala Asp Asn Lys Ala  Asn Pro Lys Ala Asp  Ser Thr Phe
    3095                 3100                 3105

Lys Met  Asp Tyr Asn Phe Asp  Val Pro Ile Ile Lys  Leu Val Gly
    3110                 3115                 3120

Lys Gly  Asn Ala Glu Thr Ile  Leu Lys Gly Glu Gly  Thr Arg Thr
    3125                 3130                 3135

Phe Ile  Ser Ala Glu Thr Leu  Ile Lys Ser Asn Ile  Asp Gly Thr
    3140                 3145                 3150

Phe Leu  Asp Arg Gly Ile Leu  Lys Gly Thr Leu Asn  Tyr Asp Glu
    3155                 3160                 3165

Ser Leu  Tyr Val Asn Gly Asn  Ser Leu Arg Tyr Ala  Leu Lys Thr
    3170                 3175                 3180

Gly Gly  Asn Gly Asp Leu Asn  Tyr Gly Asp Phe Lys  Val Ala Phe
    3185                 3190                 3195

Asp Val  Asp Glu Asn Leu Ser  Val Glu Thr Ala Asn  Glu His Val
    3200                 3205                 3210

Tyr Ala  Thr Met Lys Phe Thr  Ser Asn Asn Glu Ala  Asn Val Gly
    3215                 3220                 3225

Ser Phe  Asn Thr Lys Gly Val  His Ser Ser Gln Ala  Thr Leu Asp
    3230                 3235                 3240

Met Ala  Leu Leu Lys Ser Leu  Val Ala Asp Met Lys  Ile Asp Leu
    3245                 3250                 3255

Ser Gln  Pro Ser Thr Phe Gly  Glu Leu Ser Ile Phe  Glu Thr Met
    3260                 3265                 3270

Lys Val  Asp Leu Ser Ala Pro  Lys Gln Lys Ile Asp  Ile Leu Ser
    3275                 3280                 3285

Thr Ile  Lys Ser Pro Val Tyr  Thr Thr Asp Val Arg  Ala Lys Leu
    3290                 3295                 3300

Asp Gly  Asn Ala Pro Asp Tyr  Lys Thr Val Leu Lys  Ala Ser Ala
    3305                 3310                 3315

Thr Ser  Pro Val Val Arg Leu  Gln Tyr Asp Leu Asp  Ser Ser Met
    3320                 3325                 3330

Ser Ser  Thr Met Glu Asn Gly  Ala Leu Val Val Gly  Ala Asn Ala
    3335                 3340                 3345

Val Leu  Thr His Gln Asp Phe  Thr Met Asp Ile Ser  Asn Ala Ile
    3350                 3355                 3360

Arg Met  Ser Glu Arg Ser His  Ile Leu Asn Val Asp  Ile Thr Ser
    3365                 3370                 3375

Gln Thr  Phe Thr Asp Val Asn  Leu Arg Tyr Ala Ala  Arg Ser Asp
    3380                 3385                 3390

Gly Ile  Ser Gly Ser Val Ser  Thr Pro Gly Ser Gly  Leu Leu Gly
    3395                 3400                 3405

Phe Gln  Leu Gln Gly Asn Ile  Pro Ser Gln Met Asn  Ala Arg Leu
    3410                 3415                 3420
```

```
Tyr Cys  Arg Tyr Ala Phe Ala  Pro Asp Asp Asp Val  Asp Ile Leu
    3425                 3430                 3435

Ser Val  Arg Ala Val Pro Lys  Gly Asp Glu Lys Val  Leu Leu Val
    3440                 3445                 3450

Thr Gly  Asn Ile Lys Ala Ala  Gln Ser Met Phe Glu  Gly Leu Met
    3455                 3460                 3465

Asn Thr  Leu Glu Lys Ile Ser  Phe Lys Leu Ala Gly  Leu Ala Arg
    3470                 3475                 3480

Glu Tyr  Gly Leu Ala Phe Pro  Ile Phe Val Ala Asp  Asp Val Tyr
    3485                 3490                 3495

Gly Val  Ile Ser Asn Gly Leu  Ser Ala Ala Arg Arg  Ala Thr Pro
    3500                 3505                 3510

Gly Val  Ser Glu Leu Ser Gln  Leu Phe Arg Asn Val  Val Val Thr
    3515                 3520                 3525

Ser Gln  Lys Thr Ile Gln Val  Leu Ile Asp Asn Ala  Ile Val Leu
    3530                 3535                 3540

Val Lys  Glu Ile Ser Gln Tyr  Lys Leu Pro Gly Met  Asn Glu Ala
    3545                 3550                 3555

Thr Leu  Ala Glu Ile Cys Lys  Lys Ile Gln Leu Val  Val Val Glu
    3560                 3565                 3570

Met Leu  Arg Asn Phe Gly Asn  Asn Leu Glu Val Tyr  Phe Ser Pro
    3575                 3580                 3585

Ile Met  Asp Asn Phe Asn Thr  Ile Gln Leu Thr Phe  Pro Asn Gly
    3590                 3595                 3600

Lys Val  Met Thr Val Ala Glu  Phe Gln Gln Asn Val  Gln Ser Ile
    3605                 3610                 3615

Leu Arg  Ser Asn Leu Val Met  Ile Ala Asp Ala Met  Lys Gln Ile
    3620                 3625                 3630

Glu Ser  Pro Asp Val Val Leu  Lys Lys Leu Gly Gln  Thr Leu Gln
    3635                 3640                 3645

Glu Val  Val Glu Lys Gly Gln  Glu Phe Val Asp Lys  Met Asn Leu
    3650                 3655                 3660

Ser Leu  Leu Glu Asp Ile Ala  Ala Ala Ile Asn Thr  Phe Tyr Leu
    3665                 3670                 3675

Glu Leu  Met Lys Ile Ile Glu  Asp Ile Ser Glu Ala  Val Met Phe
    3680                 3685                 3690

Gly Phe  Ser Ile Pro Ala Ile  Lys Ile Tyr Glu Met  Ser Gln Asn
    3695                 3700                 3705

Ile Glu  Lys Val Leu Asn Ala  Asn Asn Gly Ile His  Gln Phe Glu
    3710                 3715                 3720

Leu Pro  Leu Pro Phe Phe Gln  Thr Ser Leu Tyr Lys  Lys Ala Gly
    3725                 3730                 3735

Leu Met  Val Phe Thr Leu Glu  Asp Phe Val Gly Asp  Trp Arg Gln
    3740                 3745                 3750

Thr Ala  Gly Tyr Asn Leu Asp  Gln Val Leu Glu Gln  Gly Gly Val
    3755                 3760                 3765

Ser Ser  Leu Phe Gln Asn Leu  Gly Val Ser Val Thr  Pro Ile Gln
    3770                 3775                 3780

Arg Ile  Val Leu Ser Gly Glu  Asn Gly Leu Lys Ile  Asp Ile His
    3785                 3790                 3795

Val Ile  Ile Pro Tyr Glu Gly  Leu Ser Gly Asp Gln  Met Gly Gln
    3800                 3805                 3810
```

```
Ile Glu  Lys Ile Phe Lys Val  Val Tyr Pro Val Asp  Asp His His
    3815                 3820                 3825

Phe Lys  Val Ile Leu His Tyr  Gly Thr Leu Val Ile  Asp Gly Val
    3830                 3835                 3840

Thr Pro  Asn Met Ile Asp Tyr  Phe Gly Arg Pro Tyr  Glu Gly Ile
    3845                 3850                 3855

Ala Val  Phe Asp Gly Lys Lys  Ile Thr Val Thr Gly  Thr Leu Trp
    3860                 3865                 3870

Asn Gly  Asn Lys Ile Ile Asp  Glu Arg Leu Ile Asn  Pro Asp Gly
    3875                 3880                 3885

Ser Leu  Leu Phe Arg Val Thr  Ile Asn Gly Val Thr  Gly Trp Arg
    3890                 3895                 3900

Leu Cys  Glu Arg Ile Leu Ala
    3905                 3910
```

<210> SEQ ID NO 3
<211> LENGTH: 15896
<212> TYPE: DNA
<213> ORGANISM: Danio rerio

<400> SEQUENCE: 3

```
atggggggga ctaagctctg ccttttgcta cttctatgtg caattgcctt gtcatgtaag     60
tactactaaa gatttgtatc ttatggaaat tgctattttt gtataataaa aacaatagca    120
ggatgtgtaa aagcgctctt ttgttttagc tggctttatt cggtttttttg tctatgtgtg    180
tgattgcttt tgcttgaaaa tatctgaatt aattgatatc aatacataaa gctaacggaa    240
aagaaatgaa ttctcaggtt ctctgaattt aaaatttata gttatgtgtt ccgagttaaa    300
ttactttttt ttttaattct gtaaactact gatgacattt cttcccaatt taaaatagaa    360
gtgttgtcac tcagagactt attttgtttg ttgtttaaaa taaaatcaaa aataaaaata    420
aagtccatgt tttcagatgt ttataataat taaagacata gaaataccaa tattctaact    480
tcagacgagt tcaccaaaat ctgtatttgc tgagataatc cagattttga tgaaaaatta    540
agactttttt tgttttgtca ttttgtaaaa aaataaataa ataatgccct aaatgataaa    600
tataaaaaaa atacataata tatttctatg gaatttggaa ggaaattttc tgagaccttt    660
attgcataaa acaaatttc aagtagtcaa ctgatttttt tccagagcta tagttaaaaa    720
gcattatata tatatatata tatatatata tatataatta taaattacat ttgtaaatta    780
aatattgttg tatgtgttgt taaagaataa cactaaattg tatgattatg gtcatttatg    840
ttatttgtat aaccttgtta tttctcatct tagatgcaca agaggaagaa ccatgccttt    900
gtaagtccca agctattaat atattcaaga aaaattgaat gattttgtct ctaagaaatt    960
taatgtagct tatgtgacca aataatattt taccaataaa ttaatgaaac aacaaaaatg   1020
ttatgtcctt taaattttga gttactgatg catgaaactg gatttataac tgaagacttc   1080
acctcagaac agctatctaa tcatgtaaat gacagtcatg tatgagcctc cttgatgttt   1140
atgatgtgat ttgtgctccc ccagtggcca aaaggttcaa gagctttcag aagtatgaat   1200
acacctacga aacggagtct ctaaatgccc tgaatggagc aatcaatggt cccaaggcca   1260
gatgcaaggt ataaatgttc acactattac gttttaatta aatgtaaaac atttatattt   1320
taaaatttaa attttaatac atattctatt tttgaacagg ttgaaattga ggtcccacgc   1380
atatgcagct atatcgttca cacaactgag tgtgagttga gtgatgtcat cgatgttgat   1440
gctgaaggaa agcctatctt tatgtcatct gctggtgcag aggctttcaa ggctgccatg   1500
```

```
gcaaagtaag attctcaagg catacagtca aacagtgaca agatagagga agcaaatagt   1560
attaaataaa tactgaccta ccatcatctg gttttcagga accccctgaa gttcaccgtt   1620
gagggagata atgacatcaa gttgtttcct gagaatgatg aaccagccaa cattttgaac   1680
ttcaaaagag gtctaatctc agcccttgca gcacctgtgc tggaggaaga cagaaacagg   1740
agaatggtca gtcattaact caaaactcaa atatacagta cacgtgttaa aactgattta   1800
cattgactga tccattccaa ttttgtctca aaaccagccc accgtctacg gcatgtgcag   1860
gacagactac tctgtgaatg ccagacagga tattgccacc gatgttgtcc tcaacagaga   1920
cttgtctaac tgtgacaaat tcagcccagt caaagaccac actagtcccc tggcacttat   1980
cacaggaatg gtaagtcatc ccatctttaa aaacacacac acaaaacaat gtttgctgga   2040
tagcttctga aaaagatgtc aaccttgctt gtttttatca tcacacagca atacccactt   2100
gctcagctca tcagaagcag ccaaacctgc aactacaagt ttgacaatga tcaaaagcat   2160
atgacctcgg cttcttgctc tgaaaaacac atgcttttgc cattttctta caagtgagtt   2220
cattgacaac tatgtgagtt tgtacttttt gcctggctgt ttcttttatc actctgctaa   2280
ttaattttga ttatcaacag aggagagcat ggcgtttcta atgtaggaaa gcaagctttg   2340
actctggtgg gagtgtctgt atacaacggc agaatctttg accacagtaa gtaatcattc   2400
ttacatttga attggctttc attttgcact gatcagaaga aatccaattc tcttcattta   2460
cccacttcta gatgaagcca acatgaagac cctgcatctt gatgacagca ttgactcagt   2520
ccatccaatt caagacaaag atgcaatcct gtcaattcta agggacctga atgacctttc   2580
tgagaccaca aatggagaaa atagagccca tcttgctcac aaactcattt ctaccatccg   2640
caaaatgagt gcagaaagcc tgagtgctgc tctgccagag gcactggaga tttctcgccc   2700
ccttgtgtac caagctttgt tccagtgtgg cactcctgaa tgcaccagtg ccatcctgcg   2760
ggttctcaga acctttgacc gttcctctgt agagattgat gctgcagtgt atgccatggg   2820
aatggttcca aatccatcca gagaccttgt tgaggagatg ctggagatgg ccaagttcaa   2880
atctagcaag cccatctact atgctctcag caatgctgtg aagaggtaag aaaatgaaaa   2940
acgtcaatca caatcatgtt atttattcta tctacgaatt tactgaatct atggatattg   3000
gtctgtttca ttcaaggctc tatgaagttg aaaaaagtgt caccccctgag atcaaggcag   3060
tcgcagatta caccettgaa cagattggcg actgcacagg gaaccaagaa catgtgtacc   3120
tgtccctgag ggtatgttca acctgatcca ttaagcatgc ttcatcaagt taaaaataac   3180
agctgatatg tggatattga aatatgtact tgaaaacact tataggtcat tggaaacatg   3240
gctgctgctg tcggagctgc aagccctgct ctgaaatcag cagttatcca gtgcataaac   3300
caacccgctg catcccctga ggtccagcaa gctgctattc aagtatttag gctaacttct   3360
gttcctgacg aggtaaacat ataactgaaa caagtaaatg tacttatatt taaatataat   3420
tatagtagat gcatgtttgg ctaacatatt tttttctgct ttcctaacag ggcagagagg   3480
tgctaatgaa ggtcattttc gacaaagctg ctccaataca gaagcgtgtt gctgcgtatc   3540
tcattgtgat gaaggaccct cagcccactg aactggctca gctggttgca gctctgccta   3600
ataataaaaa ctgccaggct atgagctttg ttaactcaca tctccggaac atcctgagct   3660
ctacaacatc agagaccggg gagtgagtat acatattcat gcattttaac atcttgtgtt   3720
taaaaacatg ttctaattta ttttctgctt ctcagactca gagtaaagat tcttaatgcc   3780
ctgcaaggaa atgagatcag tacttccacc gatccaacaa aattctctcg caattacaag   3840
attggctctc tagagggaaa tgtgattttt gagtctgaag aacttctgcc caatgaagtc   3900
```

```
atcctggaga tgaccctaaa tgcctttgga tatgatgttg acatgtttga ggtacacgat   3960
tatctcactt tttcaaatat tagttttctc tttgttaaaa accaggacgt taataggttt   4020
caactttttg tttatactta cagattgggt taaacggaaa gggtctggaa cccactgttg   4080
atgccctgat tggtattgat ggattcttcc gtgacaccat gcagaagacc attaactatg   4140
cagctgacaa agtaccaagg ggcaatgaca ttatgcagag catgttccca accctatgga   4200
ataacatcaa aatgcaaaag gtctataaaa tagagtttat tctttatttc cacactgatg   4260
gcatcttttt ttgttcgatt tctcactcat gttctcctct cactctaggc ccctcaaagc   4320
attgtcaaag aaataacaaa taatgttaac aagctcatcc agaagctgaa ggttcaggac   4380
aacccagagg ctatgatcta cctgaggctt ttgggtgctg aaatgggcta tctcaaaact   4440
aatgatgtag aagacatggc ctactctgct gccttgctga ctaaaagcct cctaaatatg   4500
ttccctactg atgtaagtca actgctttaa aaaatgtgtt tagaaaatct gcccatataa   4560
caaataacaa atatatatat tttttgttta acagttccta aggaacctat actcaagtgt   4620
caacaacaac cttttccttc actacgtctt catggacaat gagttttatc taccaactgg   4680
taccggcatt cctctaagag ttgccctgtc tggtactttt gctcctggag tgaagggagg   4740
actgaaactt gctcgtgaca tggtatggat cagcctttta ttttaaccaa gctttttttc   4800
caggctagaa ctggttactt aagctaattc ttggtctatt tacacagagc gaagtggctt   4860
tcatgccatc cgctggagtt gagtttgtga cggaggttgg agctctccta cctgaatatg   4920
ttgagtctgg cctggagatg catactaaca tctaccacga gagtggtctc aaagtaaaag   4980
ttgcagtgac caataagcag ttcaagttga ccattcccac accaaaaact tcaacaaaac   5040
tcatcagtgt ctcgtaagat gcttctattt atacagaaaa gatcacaatc aacaacaaaa   5100
aaaattatct tgctctacac atgcattgca ttgatttagt attttgtttt ctctgtacag   5160
aaactcattg tattcagtga ctggtacaga aatcaagagg attcctccac tggcagagca   5220
tgtgaaagca aggaagtgca ctcctttcat tcctggtttt cagtactgcg gtgtcatgca   5280
atattctaat gccttttcca acgatgccgc tccctacttc cctttgactg gtgatagcaa   5340
gtaagcgaaa cactgggcat aatcacgggg taaatttgtt tggttacttt cttctttctg   5400
aactctaaat actaaacact gacctttacc tagatttgcc attgagatcc acccgactgg   5460
tgaggtttct tcatacacag caactgctga ttatgcatat gatggcaaag atgacacagt   5520
gacatttggt ctgaaggcag aaggtaaaac attgttttac caaataatcc cttatgatct   5580
ctacacattt ttattgaata ccctgcaact gaaatgctgc aaattttcgt tcaataggaa   5640
taacatttga gagcatagtc aaactaacat tcgacagaca gaattatgaa gtctcggctg   5700
acgtccaaat tcctgactat gacctggaag ctggaattcg ggttcatgct gttgatcgaa   5760
aagctcagag tgatgccaca cattccatcc agattgactt gatgaagaag aatgtacctg   5820
aagcatctct cattggtctt gctaagtatg cacatagttt atattaaata cattatatat   5880
atatatatat atatatatat atatatatat atatatatat atatatatat atatatatat   5940
atatatatat agtttaactt tatatatgat aattttaatt attctcaatt aatttttcat   6000
tctttaggat tgggtcaatg aaggatgcca tgctgcaggt tcagctgctc attccaaatt   6060
ttgagactga tgctaaagta acggcaacac taaaaaatac tgatgaactt aaagtggaac   6120
ttgaaagtga cataaagctt cctgagatga cctcctctat tcagaaaatg attctgaaat   6180
atggtaatta aataaataaa tatgtaaata gatctcctgt acaaaaagtg aatgtatgtc   6240
aagtcagcat tttaaaagat cttaacttaa atttgttcaa atttagtaag taaacaggaa   6300
```

-continued

```
gtcctctgcc ttttaattca ttttcatgta ctttttagat gctgaggaaa ttgaggctga   6360
ggtctcttct gatgtcacca ctgagattca caacattata actactgatg ccatcaaagc   6420
cacattcaat gatattcttg accaagaaat tggcacatct gataagaaga tccgtgatgt   6480
cttgacccaa tttgttgagg taaatgtaaa ataaatcctt atttccccaa acccatgaac   6540
ttatacagac tttttaaaaa tataatattt tttccataat catctaggct tcaaatgcct   6600
acctggagca attttctccc aacattccat atgtacagga attgaggatt cctgctctcc   6660
cagaattcac tttccctaag aagctgttcc tgaatgcgtg agtgattcag aaacagctaa   6720
actaatttta aatgcagaac cattatgaat tataaatgtt ttgttacaca ttgtactaat   6780
ttatgacatt acattaatta aaaaatattc tgtattttaa cagtgagggt gctgctaaat   6840
acaagtttgg ccagaattat tacaccataa ccatacctgt tcctcttggt ggaaaaactt   6900
caagagattt caacctccct gctgctctgg aaacaccagt actgaacgta ccacagcttg   6960
accttcaggt taaatccatt aatatcccac ttccagtgtt ctttatacca gagagtctgt   7020
ctctgtcact acctcttgtg gcaaaggcgg aggtgtccag caagctgagc agcaacttct   7080
atgacatgga agcaaaagct tctgcaggga gtgaacttgt agataaacca acctattctg   7140
ccatgattga agtcacagga acaagtccag tggatctact ctccttcaaa atagaaggta   7200
cttgtatgct ttcatatttt ctgttaatca ctttttttgta atctgtaaaa aataaatatt   7260
gaatgttgtt ctgtttatgt ttaggatcaa ccttcctggt aggtagactt ggagaatctt   7320
tgaagactga gatgaaatcc tcccttaatc acaagctcct tgaagccagt gtcaattatt   7380
ttgaggaaat aacaactgga gaaaaaatca caatgaaatc aagcagcaag atggaggcga   7440
aaagtccctt tggtctgaag atttctctgg aacacacggg ccaggttgga ctcgatgaag   7500
atgagatctc tggagatgga aatctgttgg gctctatcaa ggctggtcct ttgaatggtg   7560
aagttgctct cagacaatca cttatccttc ttccattcaa gccagagctg aaaatcgact   7620
cttctctgaa agtagactta gaacaaatcc aagcagagaa cataattgaa gcagcttttg   7680
ccaatggaga gctctctttc acatctaaat caacagcatt ccaggacaat ctcatacatg   7740
ttgctgaact tgcctataaa gaatcacagc ttgctctgaa gtcagatgca agggcaaagg   7800
ctttcggcct aaacatccaa aatgtagctg aggctagtgc tagttttaat ttagttaacg   7860
ttaagattga cactaatgtt gacactttgt ttggaaatcg tgtccgttcc cagtttatag   7920
cagcactgga cgccaatggg ctggatgtaa aaagtgatgc ctctgcaaat ctggatgaac   7980
acacagcttc tcacatgtgc agcctttccc tgaccagaaa cggcctagtc acaattggct   8040
caaccttact agagtgccca gacatgcctt tgacactgca gaacaaattc aatggagccc   8100
ttgacacttc agggctttca ttgtcagttg aaacaaaagg taaattcgtt gaagtgacaa   8160
ttgaaaacac aaattctctg tctgcctccc tgtcctcagt agatttcatt tccaaagcta   8220
atagcgatga tggaacatat gtgcatgact tctcccttca gcttcagcca tatagtacct   8280
cgttgaaaat tagcaataat ctgaatgctc tgaacatcaa actgattaat gaggcacagt   8340
ttaaggcact tccatatgca gcagatctga ctggcagttg gaagctttcc tctggaacag   8400
atgagcttaa gaacacatat gagatcaaat atgaagatct ggttgctaca gccaagtgtg   8460
gtctcactgg aaaactcatg ggatctcaca tgagccaaaa cacagaaatt gaagttgctg   8520
gactttcagt tacatacggc agtgaatcca atttcaactc acagtatctc cgcttcaata   8580
gcgacttaca tgccgctgct gttcccttca gattcaacgt tgatgcaatg gtcaatgcag   8640
atggggattt gtatctgtat ggaaaacaaa gcgcacaagt ctactctaaa ttccttatga   8700
```

-continued

```
aggcagaacc acttgctttt gcacactcac atgaatgcag agtctcaaca acttacaacc   8760
tgtatgatga tctggtattc gaaaccaacc ttgataataa aattgatact gtgctgacac   8820
cgtctgagca aaaggccaca gtgagagtaa aatctaagtt caacaaccat gagtttaaca   8880
aagacttgag tgcttacaat acccctgaaa gacttggagt tgaaatgtct ggatccatca   8940
tcaccaacat cttcaataca gttgactctg acaatcaaga ccactttttc tctgccttcc   9000
taaaatatga taaaaacagc aacagccgtg ccttaagtct gccatttatt gatgagtttc   9060
catttgacct gcaacacatg aaacttgcag ttttgaggat tgttgaggcc atgcagagtt   9120
atatcaacag agaagaaatc attgtagaaa ttcagaaact ggccacatat gttagtgact   9180
ttgtgaatga actgaatctg gaagagaaaa tcataaaatt cagcaaggac ctgactgcgc   9240
tgtatgagga ctatggaatt actctcgacg acctggaggc ttctctgatg aatctaaagc   9300
ctgttttgtt gaagctagtc actgaacttg acacttatgt agtagagata gaaaagattg   9360
tgagggaaat aattacaagt ggcacaccat ctgatgctgc aatacagagg tttacagata   9420
tcctgaattc attcaatgag aaatatgacg tcaaagccat tgttctcact gttattgagg   9480
ctattgaaaa atttcttagg gaaatcgatg taatgagtat aaagggcagc agggaagtct   9540
tcaagcaata tgttgatgaa tattttgcta ttaaatccaa agtggaggaa attttgagtg   9600
aactgaagca gtttgttgca aactttgacc aagaaaagtt cactgaggat gtgaagaact   9660
ttgttacctc agccagattc agagactatg cagacaatct ggtggctaaa atcccaacag   9720
agcaaatcag caagattctt gaaaaagcaa aacaactgct taatctactg ggtaacagaa   9780
tgaatgccat ctatacaaat gtgagagaaa ttctggtgaa atctggggtt gacaagaaga   9840
tcgaaactct cctcaaaaaa gttgttgagc ttatcaagaa gttcaacatt gaagaaactg   9900
ttaagactct tgcggacact ttgaaatcta ttctgacccc tgtcactgag ctggtggata   9960
aggccatcaa ctacttgaaa acaacagagg caaaggaaat cattgaagat ctgaacaact  10020
gcctaaacca ctgcattaaa tatattagat catttgacta caacgcattt gtggatgagg  10080
ccaatcagaa aatcaagaag ttaacaaatg atctttacac catgagtttg tcacttgaaa  10140
tccgtcaaaa gcttgaggca atcagagagt ttgttaacta tgctttgtca tctatgagcg  10200
cttgcatcga aaagctggaa aaagtcaaag ttgtggatgt cgtcaaaaaa ttcagtgaca  10260
ttgtcgatag tgtagtcttc attgacaccg aggcactcat tgaggacctt aggaaaatac  10320
ttgcagacat tgatatcaga gaagaaatcc agaagtttct gaagcacgca agtagcatct  10380
ccaccaaggt tgtgaccact gcaacagatg catgcagtgc tgttatgcaa gtgatccaaa  10440
acatccttaa agatcaagca gttgtcaacg agctgaagca aatctgtgac agagtcaaaa  10500
cagtactgag aacagctgaa tttaagattc catctttcat ttttccactg actgaccttg  10560
ttgtgccatc cataaaaata agcttaaaga atcttcagga aatcaacctc ccatcttcac  10620
tgattgacct tccagggttt acaattctgc aatattacac tgtgccacca atcagagtag  10680
aatatgctga catcaagcag ggactattag atctcctgca cttcattgcg aactttgaaa  10740
taatgccagc tgtcgagaac atctttggtg accttagaat tgtctacatg cctgacatct  10800
ctgccatcac actgccagag ataagcttac cagagatctc tctcccagaa attcctaaat  10860
acatcagcaa gcacaaattt tctgatctga caatcccaga attcaccctc cctggagttc  10920
ctactgaggt catggtgcca tgctttggaa agttgtatgg tgaggttaga gtcaccattc  10980
caattttcaa catgagaact acagtagaat tcctaaactc tactgaaagt gcagaaaccc  11040
ctcagtttgt agggcacatt acctcacatg gatcttcaga atatgacctt cttaaataca  11100
```

-continued

```
ccttggactc cacagctcgt gttgccatgc ctaaaatgag tcgtgtgatt cttgcagaaa  11160
ccctgaagat cactcacagt gtactagcca ttgaccatca atcctcagtc tcactttatg  11220
gcctctcagc ccaggcttct tccaagagca ccatgaagat tacctcttcc acctataatg  11280
ctaacatcgt taacactgct ttctttgccc tggcaggtgg aatatctgca aatatcaaaa  11340
caacatataa tgacaagtta aatgcagacc tttggaacag tgaatattat tacggtaatg  11400
atataattct aaagcaggat ggtctaaaac tccttctgac catggaagaa gaggccaagg  11460
gacatatatc tgtgctcgaa aagtctgatg atatcactgg caagagtagt tcatctataa  11520
ttattactcc aacaacattc tctctgatca tttctgtgga ttccagcagt tctgtttcaa  11580
acattaaaaa aagtattaaa gctgacggtg ttgctctgag ctatgtcgac ttcactgcca  11640
gcattgaagg aactagtgat tctgagttat ttttactgaa tgcagctgga aaggcggatc  11700
tcagacaaat gaaagtagag atgaaggctg accttgacac aaaatatgct ggactgctca  11760
gtggtacctt caccagtgcc tttaacttct tagtgcaacc ttttgaggta gtccttgatt  11820
tcaagaacaa ggctaatact aagctcaacc ttgtagagcc cctgtctgct aagattgatc  11880
ttcagaacaa ttatactgtc atccttaata gcgacgagca gatgttgagc actgggttac  11940
ttgcccgctt taaccagtac aagtacagtc acaatttcac attggccaac aacgaggatg  12000
aggctggcat ttatgctgca gtaaatggcg aggctaattt ggaattccta acaatccctt  12060
tcagtattcc agcaatggaa ttagaaacac taactatggt aattgaaatt ccagaaatca  12120
gtaacatcaa tctatatgaa cagactgggc ttaagcatgt tttgactgac ttcgaccagg  12180
ccattgatgt agatgcaaag atggtttacc agaagaatga cttaacctct gagttgtctt  12240
tcaagtcctc catattcaat cttaatgcca atgctggttt ctatcagaag gataaccctg  12300
taattcgttt tggagtcatc actgcttctg agtttgagtc actgaaggcc aagcttgaag  12360
gaaccagcag tctgagcacc aaaagtggat tcaaattagc caattctttg cttctagaaa  12420
atcgccacat tgaaggaacc catgaaagca ctgcaactat gaacctgaat aactttgaag  12480
ttacactgtc tatggccaca gatgcaaaaa tgaatctacc aattcttaca gctaatgcca  12540
accaccaact tactgctgac aacaaggcca acccaaaagc agactcaaca tttaagatgg  12600
attacaactt tgacgttccc attattaagc ttgttggaaa gggaaatgct gaaaccatct  12660
taaaaggcga aggaactcgt acgtttatct ctgctgagac acttataaag agcaatattg  12720
atggaacatt cctagatcgt ggtattttga aaggaactct gaattacgat gaatccctgt  12780
atgtgaatgg taatagtttg cgatatgccc ttaagactgg tggtaatgga gacctgaact  12840
atggtgattt caaggtggct tttgatgtgg atgaaaacct gtctgtagag acagccaatg  12900
agcacgtata tgctacaatg aagtttactt ccaataatga agcaaatgtt ggatctttca  12960
acactaaagg agttcattcc agccaggcta ctctcgatat ggctcttctg aagtcactgg  13020
tggctgatat gaaaatagac ttgtctcaac cgagcacctt tggtgaactt agcatcttcg  13080
agacaatgaa agtagatctc agtgctccca agcagaaaat tgatatcctt tcaacaatca  13140
agtctccggt atacaccaca gatgttcgtg ctaaactaga cggtaatgcc ccagattaca  13200
aaacggttct gaaggcttca gccacttcac cagttgtgcg cctgcagtat gatcttgaca  13260
gtaagtttca acatatacta tatgtacaat gatactcaat gttaataaaa ggaaattaaa  13320
tcttggattt gtgtgctttt acacaaaaca ggctccatga gttctactat ggagaatggt  13380
gcccttgttg tcggagctaa cgctgtactt acacatcagg acttcactat ggatatcagc  13440
aatgctattc gcatgaggta aataaaaaat ctttctgatt ttttgtttga atattagtac  13500
```

```
tatgtttgca attataattt attttataaa gcaattctga gtgtaaatct aaattctact  13560
tatcattagc gaaaggagcc atattctgaa tgtggacatc accagccaaa catttaccga  13620
tgttaacctt cgctatgctg ctcggagtga tgggataagt ggctctgttt ccacaccggg  13680
gtctggcctc cttggctttc agctccaagg aaatattcca tcccaaatga atgcaaggct  13740
ctactgtcgt tatgctgtaa gttgcagttt ttttgtcttg tttttcagat aataattcat  13800
gcgtactctt tgttctcttt gtttcctgct tgcacttatt taatattcat atgtgtaata  13860
ttggtaaggt ttctaaaatt ataattgttg tattttctgc agtttgcacc agatgatgat  13920
gtcgacatcc taagcgtcag agccgtacca aagggagatg aaaaagtact gttggtcact  13980
ggcaatataa aggctgcaca atccatgttt gaaggcttaa tgaatactct agaaaaaatc  14040
tcatttaaac ttgcaggatt agcaagagaa tatggtctcg cttttccaat ttttgttgct  14100
gacgatgttt atggagtaat ttcaaatgga ctctctgctg cccgcagagc tacaccaggc  14160
gttagtgagt tatcccaact tttcagaaat gtagttgtca catcccaaaa gaccatccag  14220
gtcttgattg acaatgccat cgtactcgta aaagagattt cacaatataa actgcctgga  14280
atgaatgaag ctacactggc tgaaatttgc aagaaaatcc aattagttgt tgtagaaatg  14340
ctgaggaatt ttggtaacaa cttggaggta tacttctctc ccatcatgga taactttaat  14400
acaattcaat tgacatttcc caatggaaag gtcatgacag tagctgagtt ccaacaaaat  14460
gtgcagagta tcctgagaag caacctagtt atgatagcag atgcaatgaa gcaaatcgaa  14520
agtcctgatg tagttcttaa gaaacttgga caaactttac aagaggttgt tgaaaaagga  14580
caagagtttg tggacaaaat gaatttaagt ttattagaag atattgccgc ggccattaac  14640
acgttctacc tggagctcat gaagatcata gaagacatta gtgaggcagt catgtttggt  14700
ttttcaatcc ctgcaattaa aatatatgaa atgtctcaaa acatagagaa agtgttgaac  14760
gcaaataatg gaatacatca atttgagctt cctctcccat tttccagac  aagtttgtac  14820
aaaaaagcag gcttgatggt cttcacactc gaagatttcg ttggggactg gcgacagaca  14880
gccggctaca acctggacca agtccttgaa cagggaggtg tgtccagttt gtttcagaat  14940
ctcggggtgt ccgtaactcc gatccaaagg attgtcctga gcggtgaaaa tgggctgaag  15000
atcgacatcc atgtcatcat cccgtatgaa ggtctgagcg gcgaccaaat gggccagatc  15060
gaaaaaattt ttaaggtggt gtaccctgtg gatgatcatc actttaaggt gatcctgcac  15120
tatggcacac tggtaatcga cggggttacg ccgaacatga tcgactattt cggacggccg  15180
tatgaaggca tcgccgtgtt cgacggcaaa aagatcactg taacagggac cctgtggaac  15240
ggcaacaaaa ttatcgacga gcgcctgatc aaccccgacg gctccctgct gttccgagta  15300
accatcaacg gagtgaccgg ctggcggctg tgcgaacgca ttctggcgta aacccagctt  15360
tcttgtacaa agtggaatat ggtcattctg aacagaaagt aaactaagta aacactacca  15420
tattttgaaa tgaacattct tggacatcga agccaatgga cacttcactg aagtatagta  15480
caaacatgta tataaagcaa ttactgactc aaaacatgtc tcattgttat gctgctctat  15540
tattctattt gtataaatga ggattgaaat actaagctag ttatcaaaaa tgccacctgc  15600
aacctattgt catccttgtt ctgtatccaa cattaatggc atgatggatg gggatcaata  15660
aagaactttt attatgcaac acgacccaat cttgtcattt ctatattcta gaagtgtttt  15720
acactagttt ggaccattca ataatataat ataattgaat atacaggtgt aataacatgc  15780
```

-continued

```
aacaaaatgt aaaataagca gtggtacatg ggtacatttt agttttttat gcaaactact  15840

ggtgacttta aaaaaaaaat tacaaataaa atattttatt ctattttttt cattag      15896
```